US009024751B2

(12) United States Patent
Duesterhoft et al.

(10) Patent No.: US 9,024,751 B2
(45) Date of Patent: May 5, 2015

(54) DORMANT TO ACTIVE APPURTENANCES FOR REPORTING INFORMATION REGARDING WOUND DRESSINGS

(75) Inventors: Paul Duesterhoft, Issaquah, WA (US); Nicholas Dykstra, Seattle, WA (US); Daniel Hawkins, Bellevue, WA (US); Roderick A. Hyde, Redmond, WA (US); Jordin T. Kare, Seattle, WA (US); Mark K. Kuiper, Seattle, WA (US); Eric C. Leuthardt, St Louis, MO (US); Nels R. Peterson, Bellevue, WA (US); Elizabeth L. Schubert, Bellevue, WA (US); Clarence T. Tegreene, Bellevue, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 366 days.

(21) Appl. No.: 13/491,677

(22) Filed: Jun. 8, 2012

(65) Prior Publication Data

US 2013/0274630 A1    Oct. 17, 2013

Related U.S. Application Data

(63) Continuation-in-part of application No. 13/445,174, filed on Apr. 12, 2012, and a continuation-in-part of application No. 13/445,220, filed on Apr. 12, 2012.

(51) Int. Cl.
| | |
|---|---|
| *G08B 1/08* | (2006.01) |
| *A61F 13/00* | (2006.01) |
| *A61B 5/01* | (2006.01) |
| *A61B 5/03* | (2006.01) |

(Continued)

(52) U.S. Cl.
CPC ............ *A61F 13/00051* (2013.01); *A61B 5/01* (2013.01); *A61B 5/03* (2013.01); *A61B 5/053* (2013.01); *A61B 5/14546* (2013.01)

(58) Field of Classification Search
USPC ......... 340/539.12, 539.22, 573.1, 572.1, 10.1
See application file for complete search history.

(56) References Cited

U.S. PATENT DOCUMENTS

| 4,384,288 A | 5/1983 | Walton |
| 5,704,352 A | 1/1998 | Tremblay et al. |

(Continued)

FOREIGN PATENT DOCUMENTS

| EP | 0 430 608 A1 | 6/1991 |
| WO | WO 00/08203 | 2/2000 |

(Continued)

OTHER PUBLICATIONS

U.S. Appl. No. 13/445,220, Duesterhoft et al.

(Continued)

*Primary Examiner* — Daryl Pope
(74) *Attorney, Agent, or Firm* — Dorsey & Whitney LLP

(57) ABSTRACT

Appurtenances to wound dressings can include: a substrate configured to attach to a wound dressing; a fluid-activated voltaic cell attached to the substrate; a transmission unit attached to a surface of the substrate, the transmission unit including circuitry and at least one antenna, the transmission unit configured to transmit a signal in response to current generated by the fluid-activated voltaic cell; and a projection operably attached to the fluid-activated voltaic cell, the projection of a size and shape to extend into an interior region of the wound dressing and configured to sample a fluid within the interior region of the wound dressing.

47 Claims, 14 Drawing Sheets

(51) Int. Cl.
*A61B 5/053* (2006.01)
*A61B 5/145* (2006.01)

(56) References Cited

U.S. PATENT DOCUMENTS

| | | | |
|---|---|---|---|
| 5,904,671 | A | 5/1999 | Navot et al. |
| 5,912,114 | A | 6/1999 | Hutchinson et al. |
| 5,939,205 | A | 8/1999 | Yokoyama et al. |
| 6,037,879 | A | 3/2000 | Tuttle |
| 6,270,455 | B1 | 8/2001 | Brown |
| 6,283,938 | B1 | 9/2001 | McConnell |
| 6,348,640 | B1 | 2/2002 | Navot et al. |
| 6,420,622 | B1 | 7/2002 | Johnston et al. |
| 6,693,513 | B2 | 2/2004 | Tuttle |
| 6,863,220 | B2 | 3/2005 | Selker |
| 6,889,165 | B2 | 5/2005 | Lind et al. |
| 6,963,772 | B2 | 11/2005 | Bloom et al. |
| 7,030,764 | B2 | 4/2006 | Smith et al. |
| 7,055,754 | B2 | 6/2006 | Forster |
| 7,215,976 | B2 | 5/2007 | Brideglall |
| 7,297,112 | B2 | 11/2007 | Zhou et al. |
| 7,372,780 | B1 | 5/2008 | Braunberger |
| 7,411,505 | B2 | 8/2008 | Smith et al. |
| 7,446,660 | B2 | 11/2008 | Posamentier |
| 7,479,886 | B2 | 1/2009 | Burr |
| 7,507,675 | B2 | 3/2009 | Zuilhof et al. |
| 7,612,424 | B1 | 11/2009 | Espinosa et al. |
| 7,666,151 | B2 | 2/2010 | Sullivan et al. |
| 7,667,606 | B2 | 2/2010 | Packert et al. |
| 7,703,334 | B2 | 4/2010 | Cochran |
| 7,724,136 | B2 | 5/2010 | Posamentier |
| 7,794,925 | B2 | 9/2010 | Cullen |
| 7,813,226 | B2 | 10/2010 | Braunberger |
| 7,825,776 | B2 | 11/2010 | Smith et al. |
| 7,914,867 | B2 | 3/2011 | Mori et al. |
| 7,945,302 | B2 | 5/2011 | McAdams |
| 7,951,605 | B2 | 5/2011 | Pitner et al. |
| 7,964,390 | B2 | 6/2011 | Rozakis et al. |
| 7,986,235 | B2 | 7/2011 | Posamentier |
| 8,014,234 | B2 | 9/2011 | Braunberger |
| 2003/0199783 | A1 | 10/2003 | Bloom et al. |
| 2003/0216663 | A1 | 11/2003 | Jersey-Willuhn et al. |
| 2006/0036145 | A1 | 2/2006 | Brister et al. |
| 2006/0047218 | A1 | 3/2006 | Bloom et al. |
| 2007/0171076 | A1 | 7/2007 | Stevens et al. |
| 2007/0204691 | A1 | 9/2007 | Bogner et al. |
| 2007/0231380 | A1 | 10/2007 | Shah et al. |
| 2007/0247316 | A1 | 10/2007 | Wildman et al. |
| 2007/0252712 | A1 | 11/2007 | Allen et al. |
| 2007/0269851 | A1 | 11/2007 | Sanders et al. |
| 2008/0166397 | A1 | 7/2008 | Trotter et al. |
| 2009/0167495 | A1 | 7/2009 | Smith et al. |
| 2009/0192369 | A1 | 7/2009 | Say et al. |
| 2009/0209883 | A1 | 8/2009 | Higgins et al. |
| 2009/0243813 | A1 | 10/2009 | Smith et al. |
| 2009/0299161 | A1 | 12/2009 | Cullen et al. |
| 2010/0022990 | A1 | 1/2010 | Karpowicz et al. |
| 2010/0030167 | A1 | 2/2010 | Thirstrup et al. |
| 2010/0100061 | A1 | 4/2010 | Odland |
| 2010/0166694 | A1 | 7/2010 | Stephens et al. |
| 2010/0204606 | A1 | 8/2010 | Kim et al. |
| 2010/0331634 | A1 | 12/2010 | Müller et al. |
| 2011/0015591 | A1 | 1/2011 | Hanson et al. |
| 2011/0054340 | A1 | 3/2011 | Russ et al. |
| 2011/0082356 | A1 | 4/2011 | Yang et al. |
| 2011/0092927 | A1 | 4/2011 | Wilkes et al. |
| 2011/0105854 | A1 | 5/2011 | Kiani et al. |
| 2011/0140703 | A1 | 6/2011 | Chiao et al. |
| 2011/0178375 | A1 | 7/2011 | Forster |
| 2011/0213559 | A1 | 9/2011 | Pollack et al. |
| 2012/0010099 | A1 | 1/2012 | Stephens et al. |
| 2012/0109034 | A1* | 5/2012 | Locke et al. ............ 602/42 |
| 2013/0261409 | A1 | 10/2013 | Pathak et al. |
| 2013/0304006 | A1 | 11/2013 | Toth |

FOREIGN PATENT DOCUMENTS

| | | |
|---|---|---|
| WO | WO 03/040406 A2 | 5/2003 |
| WO | WO 2005/009328 A1 | 2/2005 |
| WO | WO 2007/130239 A1 | 11/2007 |

OTHER PUBLICATIONS

U.S. Appl. No. 13/445,174, Duesterhoft et al.
Abhisam; "RFID systems for pharmaceutical distributors to meet the new FDA regulations on drugs"; Discover the power of e-learning!; bearing a date of 2006; pp. 1-7; Abhisam Software.
Alien Technology; "Battery Assisted Passive Tags"; Alien Technology brochure; downloaded from the web Oct. 17, 2011; pp. 1-2; located at: http://www.alientechnology.com/docs/AT_DS_BAP.pdf; Alien Technology Corp.
Berggren et al.; "Capacitive Biosensors"; Electroanalysis; bearing a date of 2001; pp. 173-180; vol. 13, No. 3; Wiley-VCH Verlag GmbH.
"Body-fluid battery"; Science News; Sep. 10, 2005; pp. 1-2; located at http://findarticles.com/p/articles/mi_m1200/is_11_168/ai_n15674798/; Science.Service, Inc. and Gale Group.
Chawla et al.; "An Overview of Passive RFID"; IEEE Applications & Practice; Sep. 2007; pp. 11-17; IEEE.
Chen et al.; "A 2G-RFID-Based E-Healthcare System"; IEEE Wireless Communications; Feb. 2010; pp. 37-43; IEEE.
Chen et al.; "Ultrasonic Measurement System with Infrared Communication Technology"; Journal of Computers; Nov. 2011; pp. 2468-2475; vol. 6, No. 11; Academy Publisher.
Collier, Mark; "Recognition and management of wound infections"; World Wide Wounds; Jan. 2004; pp. 1-9.
Cui et al.; "Nanowire Nanosensors for Highly Sensitive and Selective Detection of Biological and Chemical Species"; Science; Aug. 17, 2001; pp. 1289-1292, and 1 cover page; vol. 293; American Association for the Advancement of Science.
Cutting et al.; "Criteria for identifying wound infection"; Journal of Wound Care; Jun. 1994; pp. 198-201; vol. 3, No. 4.
Fadlullah et al; "Indoor High-Bandwidth Optical Wireless Links for Sensor Networks"; Journal of Lightwave Technology; Nov. 1, 2010; pp. 3086-3094; vol. 28, No. 21; IEEE.
Finkenzeller, Klaus; "Fundamental Operating Principles" Chapter 3 of the RFID Handbook: Fundamentals and Applications in Contactless Smart Cards and Identification; bearing a date of 2003; pp. 29-59; John Wiley & Sons, Ltd.
Fisher et al.; "Tracking the social dimensions of RFID systems in hospitals"; International Journal of Medical Informatics; bearing a date of 2008; pp. 176-183; vol. 77; Elsevier Ireland Ltd.
Fisher, Jill A.; "Indoor Positioning and Digital Management: Emerging Surveillance Regimes in Hospitals"; Chapter 5 in T. Monahan (Ed), Surveillance and Security: Technological Politics and Power in Everyday Life; May 23, 2006; pp. 77-88; Routledge.
Frost & Sullivan; "Advances in Wound Healing Techniques"; Technical Insights; Publication D11A; bearing a date of 2008; pp. 1-118; Frost & Sullivan.
Frost & Sullivan; "An Overview of Ulceration Wounds"; Publication M4BB-54; Dec. 2009; pp. 1-77; Frost & Sullivan.
Frost & Sullivan; "U.S. Advanced Wound Care Market"; Publication N71A-54; Aug. 2010; pp. 1-90; Frost & Sullivan.
Goodisman, Jerry; "Observations on Lemon Cells"; Journal of Chemical Education; Apr. 2001; pp. 516-518; vol. 78, No. 4.
Gray, David; "Assessment, Diagnosis and Treatment of Infection"; Wounds UK; bearing a date of 2011; pp. 4-9; vol. 7, No. 2, supplement.
Huang et al.; "Development of an $IrO_x$ Micro pH Sensor Array on Flexible Polymer Substrate"; Nanosensors and Microsensors for Bio-Systems 2008, edited by Vijay K. Varadan, Proc. of SPIE, vol. 6931, 693104; 2008; pp. 1-9.
Huang et al.; "Investigation of Repeatability of Sol-Gel Iridium Oxide pH Sensor on Flexible Substrate"; Micro- and Nanotechnology: Materials, Processes, Packaging, and Systems IV, edited by Jung-Chih Chiao et al., Proc. of SPIE, vol. 7269, 726916; 2008; pp. 1-9.

(56) References Cited

OTHER PUBLICATIONS

Ibridge Network; "pH Sensor Array on Flexible Substrate for Wound Care (UTA Ref. No. 08-21)"; Nov. 28, 2011; pp. 1-2; Kauffman Innovation Network, Inc.

Intel; "WISP: Wireless Identification and Sensing Platform"; Intel Labs Seattle; printed on Oct. 8, 2011; pp. 1-4; located at http://www.seattle.intel-research.net/WISP/.

Intelleflex; "Worldwide RFID UHF Map"; printed on Oct. 17, 2011; p. 1; located at: http://www.intelleflex.com/pdf/Worldwide_UHF_Chart.pdf ; Intelleflex Corporation.

Karthik MNS; "Could blood be used to power batteries?"; Feb. 2009; pp. 1-4; located at: http://hoowstuffworks.blogspot.com/2009/02/could-blood-be-used-to-power-batteries.html.

Kavehrad, Mohsen; "Sustainable Energy-Efficient Wireless Applications Using Light"; IEEE Communications Magazine; Dec. 2010; pp. 66-73; IEEE.

Kelly-Quintos et al.; "Characterization of the Opsonic and Protective Activity Against *Staphylococcus aureus* of Fully Human Monoclonal Antibodies Specific for the Bacterial Surface Polysaccharide Poly-N-Acetylglucosamine"; Infection and Immunity; May 2006; pp. 2742-2750; vol. 74, No. 5; American Society for Microbiology.

Lee et al.; "Water Activated Disposable and Long Shelf Life Microbatteries"; 2003; pp. 387-390; IEEE.

Lim et al.; "A Micromechanical Biosensor with Interdigitated Capacitor Readout"; Proceedings of the 2011 IEEE/ICME International Conference on Complex Medical Engineering; May 22-25, 2011; pp. 42-46; IEEE.

Löfgren et al.; "Low-power humidity sensor for RFID applications"; Multi-Material Micro Manufacture; 2008; 4 pages; Cardiff University.

McColl et al.; "Monitoring moisture without disturbing the wound dressing"; Wounds UK; bearing a date of 2009; pp. 94-96, and 98-99; vol. 5, No. 3.

Murata Manufacturing Co., Ltd.; "Piezoelectric Sound Components"; Cat. No. P37E-23; Nov. 2009; pp. 1-33, and two cover pages.

Murata Manufacturing Co., Ltd.; "Ultrasonic Sensor Application Manual"; Cat. No. S15E-5; Aug. 2009; pp. 1-3, and 2-14, and one supplemental page.

Nature News; "A miniature biofuel cell operating in a physiological buffer"; Nature; Nov. 12, 2002; pp. 1-2; located at http://www.nature.com/news/2002/021112/full/news021111-1.html.

Ohno et al.; "Graphene Field-Effect Transistors for Label-Free Biological Sensors"; IEEE Sensors 2010 Conference Proceedings; Nov. 1-4, 2010; pp. 903-906; IEEE.

Pacific Northwest National Laboratory; "Juvenile Salmon Acoustic Telemetry System (JSATS) Acoustic Transmitters"; Mar. 2010; pp. 1-2.

Pan et al.; "Development of the real-time pH sensing system for array sensors"; Sensors and Actuators B 108; 2005; pp. 870-876; Elsevier B.V.

Patauner et al.; "High Speed RFID/NFC at the Frequency of 13.56 MHz"; presented at the First International EURASIP Workshop on RFID Technology; Sep. 24-25, 2007; pp. 1-4.

Pushparaj et al.; "Flexible energy storage devices based on nanocomposite paper"; PNAS; Aug. 21, 2007; pp. 13574-13577; vol. 104, No. 34; The National Academy of Sciences of the USA.

Ruhanen et al.; "Sensor-enabled RFID tag handbook"; Building Radio Frequency Identification for the Global Environment; Jan. 2008; pp. 1-47; IST-2005-033546; European Commission.

Sammoura et al.; "Water-activated disposable and long shelf life microbatteries"; Sensors and Actuators A 111; 2004; pp. 79-86; Elsevier B.V.

Sample et al.; "A Capacitive Touch Interface for Passive RFID Tags"; IEEE International Conference on RFID; Apr. 27-28, 2009; pp. 103-109; IEEE.

Sample et al.; "Design of an RFID-Based Battery-Free Programmable Sensing Platform"; IEEE Transactions on Instrumentation and Measurement; Nov. 2008; pp. 2608-2615; vol. 57, No. 11; IEEE.

Sample et al.; "Photovoltaic Enhanced UHF RFID Tag Antennas for Dual Purpose Energy Harvesting"; 2011 International Conference on RFID; Apr. 12-14, 2011; pp. 146-153; IEEE.

Sidén et al.; "The 'Smart' Diaper Moisture Detection System"; IEEE MTT-S Digest, WE4B-3; 2004; pp. 659-662; IEEE.

Stevens et al.; "RuBee (IEEE 1902.1)—The Physics Behind, Real-Time, High Security Wireless Asset Visibility Networks in Harsh Environments"; Sep. 2010; retrieved from web Nov. 17, 2011; pp. 1-6; located at: http://www.rubee.com/White-SEC/RuBee-Security-080610.pdf.

Tehrani et al.; "Detection of Monoclonal Antibodies using Chemically Modified Graphite Substrates"; IEEE Sensors 2010 Conference Proceedings; Nov. 1-4, 2010; pp. 428-431; IEEE.

University of Texas Arlington, Office of Technology Management; "Smart Wound Condition Monitoring pH Sensor Array on Flexible Substrate"; Technology Summary; printed on Apr. 12, 2012; pp. 1-2.

Visible Assets; "RuBee Technology, Real-Time Asset Visibility"; printed from web Nov. 17, 2011; pp. 1-3; located at: http://www.rubee.com/Techno/index.html ;Visible Assets.

Wang, Wencheng; "A Design Method of Ultrasonic Ranging System with High Accuracy"; Journal of Computational Information Systems; Jul. 2011; pp. 2444-2451; vol. 7, No. 7; Binary Information Press.

Yeager et al.; "Wirelessly-Charged UHF Tags for Sensor Data Collection"; 2008 IEEE International Conference on RFID; Apr. 16-17, 2008; pp. 320-327; IEEE.

PCT International Search Report; International App. No. PCT/US13/36000; Jul. 5, 2013; pp. 1-3.

PCT International Search Report; International App. No. PCT/US2013/035993; Jun. 25, 2013; pp. 1-2.

U.S. Appl. No. 14/252,136, Duesterhoft et al.

U.S. Appl. No. 14/252,049, Allin et al.

DeHennis et al.; "A Wireless Microsystem for the Remote Sensing of Pressure, Temperature, and Relative Humidity"; Journal of Microelectromechanical Systems; Feb. 2005; pp. 12-22; vol. 14, No. 1; IEEE.

Mehmood et al.; "Applications of modern sensors and wireless technology in effective wound management"; Journal of Biomedical Materials Research B: Applied Biomaterials; bearing a date of Sep. 27, 2013; pp. 1-11; Wiley Periodicals, Inc.

U.S. Appl. No. 13/795,667, Duesterhoft et al.

Bluestein et al.; "Pressure Ulcers: Prevention, Evaluation, and Management"; American Family Physician; Nov. 15, 2008; pp. 1186-1194; vol. 78, No. 10; American Academy of Family Physicians.

Clay, Karen S.; "Preventing pressure ulcers in your facility: Karen S. Clay, RN, BSN, CWCN, presents a primer on how to protect frail residents—and avoid costly reprimands"; bearing a date of 2004; 14 pages; HCPro, Inc.

Dowd et al.; "Survey of bacterial diversity in chronic wounds using Pyrosequencing, DGGE, and full ribosome shotgun sequencing"; BMC Microbiology; bearing a date of 2008, published Mar. 6, 2008; pp. 1-15; vol. 8, No. 43; BioMed Central Ltd.

Grist et al.; "Optical Oxygen Sensors for Applications in Microfluidic Cell Culture"; Sensors; bearing a date of 2010, published Oct. 15, 2010; pp. 9286-9316; vol. 10; MDPI; Basel, Switzerland.

\* cited by examiner

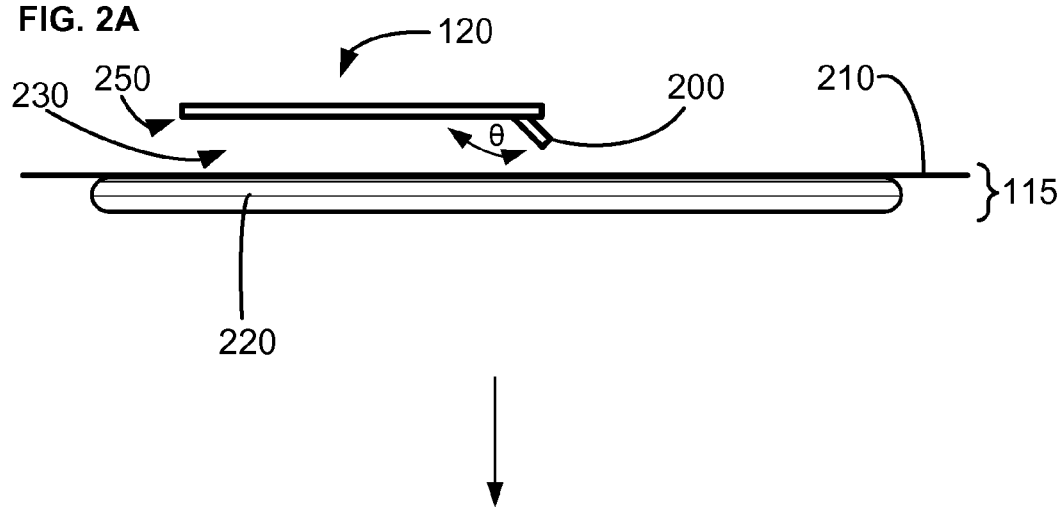
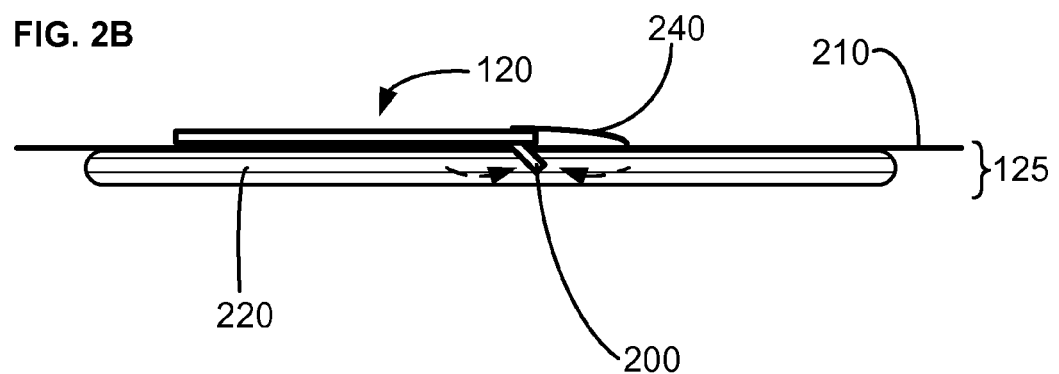

FIG. 13
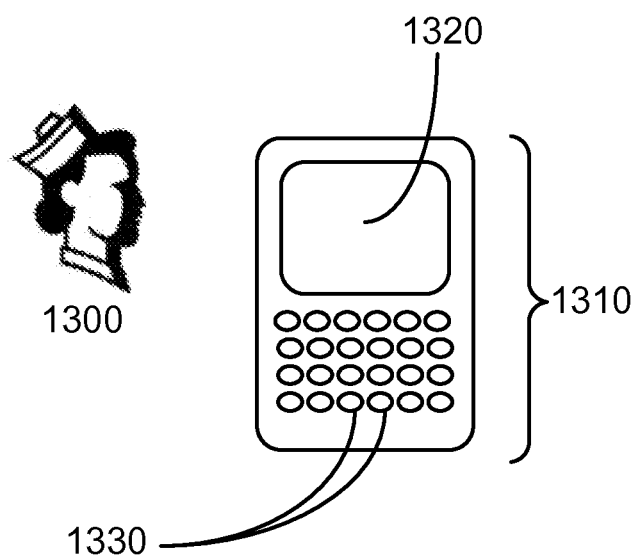
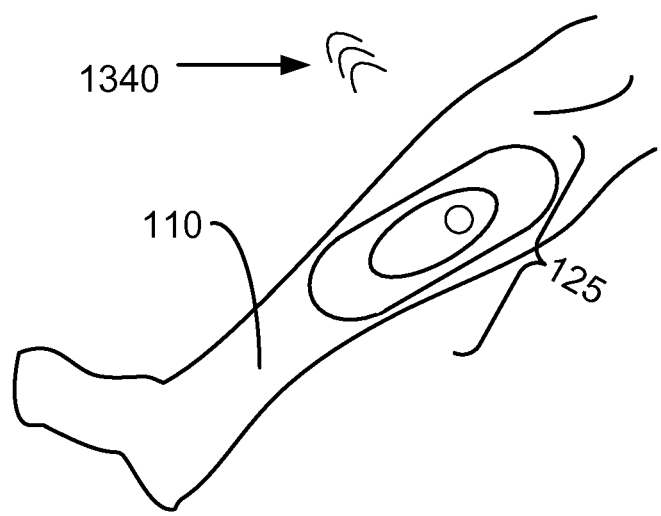

DORMANT TO ACTIVE APPURTENANCES FOR REPORTING INFORMATION REGARDING WOUND DRESSINGS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/445,174, entitled APPURTENANCES FOR REPORTING INFORMATION REGARDING WOUND DRESSINGS, naming Paul Duesterhoft, Nicholas Dykstra, Daniel Hawkins, Roderick A. Hyde, Jordin T. Kare, Eric C. Leuthardt, Elizabeth L. Schubert, Clarence T. Tegreene, and Lowell L. Wood, Jr. as inventors, filed 12 April 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/445,220, entitled COMPUTATIONAL METHODS AND SYSTEMS FOR REPORTING INFORMATION REGARDING APPURTENANCES TO WOUND DRESSINGS, naming Paul Duesterhoft, Nicholas Dykstra, Daniel Hawkins, Roderick A. Hyde, Jordin T. Kare, Eric C. Leuthardt, Elizabeth L. Schubert, Clarence T. Tegreene, and Lowell L. Wood, Jr. as inventors, filed 12 Apr. 2012, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

In one aspect, an appurtenance to a wound dressing includes, but is not limited to: a substrate configured to attach to a wound dressing; a fluid-activated voltaic cell attached to the substrate; a transmission unit attached to a surface of the substrate, the transmission unit including circuitry and at least one antenna, the transmission unit configured to transmit a signal in response to current generated by the fluid-activated voltaic cell; and a projection operably attached to the fluid-activated voltaic cell, the projection of a size and shape to extend into an interior region of the wound dressing and configured to sample a fluid within the interior region of the wound dressing.

In one aspect, an appurtenance to a wound dressing includes, but is not limited to: an enclosure of a height and width to fit substantially within an interior region of a wound dressing, the enclosure including at least one aperture configured to allow fluid to flow from the interior region of the wound dressing into the enclosure; a fluid-activated voltaic cell attached to one or more of the at least one aperture; and a transmission unit attached to an internal surface of the enclosure, the transmission unit including circuitry and at least one antenna, the transmission unit configured to transmit a signal in response to the fluid-activated voltaic cell.

In one aspect, an appurtenance to a wound dressing includes, but is not limited to: an appurtenance configured to attach to a wound dressing, the appurtenance including a conduit configured to allow fluid flow from an interior region of a wound dressing into the appurtenance; a fluid-activated voltaic cell including an internal chamber, the internal chamber attached to the conduit; and a radio frequency identification (RFID) unit attached to the fluid-activated voltaic cell and configured to operate in response to current generated by the fluid-activated voltaic cell.

In one aspect, a method of monitoring a wound includes, but is not limited to: conveying fluid from an interior region of a wound dressing to an appurtenance of the wound dressing; placing the fluid adjacent to a first electrode and a second electrode of a fluid-activated voltaic cell integral to the appurtenance; and utilizing current received from the fluid-activated voltaic cell directly to send a wireless signal beyond the appurtenance.

In addition to the foregoing, other aspects of an appurtenance to a wound dressing are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2A is a schematic of an appurtenance to a wound dressing prior to attachment to a wound dressing.

FIG. 2B is a schematic of an appurtenance to a wound dressing after attachment to a wound dressing.

FIG. 13 is a schematic of an appurtenance to a wound dressing in communication with a local unit.

DETAILED DESCRIPTION

Figure 1:
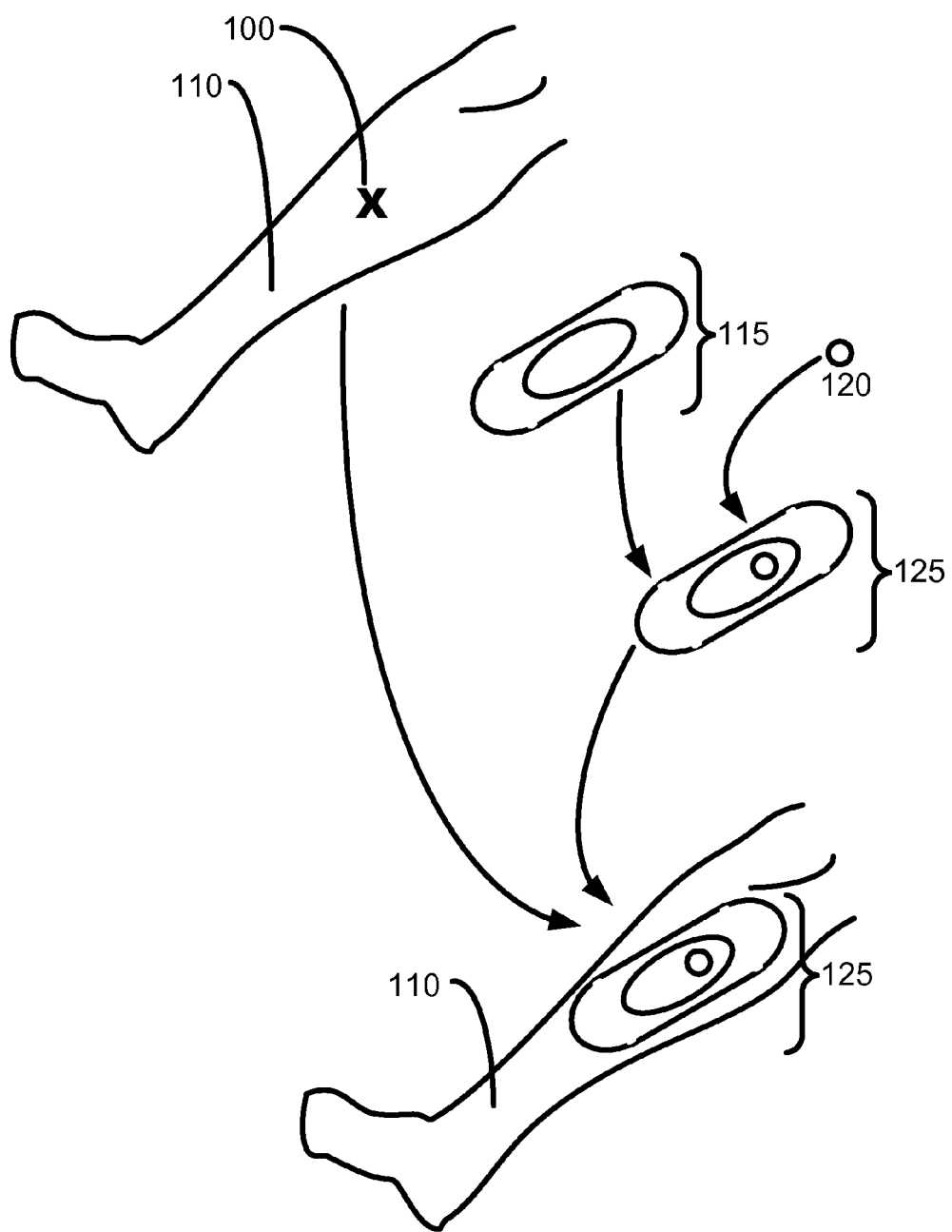
FIG. 1 is a schematic of an appurtenance to a wound dressing in use with a wound.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The use of the same symbols in different drawings typically indicates similar or identical items.

With reference now to FIG. 1, shown is an example of an appurtenance 120 to a wound dressing 115, used on a wound 100, which can serve as a context for introducing one or more processes and/or devices described herein. As shown in FIG. 1, a body part 110, such as a leg, includes a wound 100. A wound dressing 115, selected by a medical caregiver as appropriate in size, shape and type for the wound 100, has an appurtenance 120 attached to generate an appurtenance affixed to a wound dressing combination unit, 125. The appurtenance 120 can be attached to the wound dressing 115 with a mechanical attachment. For example, a mechanical attachment can include mechanical attachment features shaped like prongs, barbs, bristles, spikes, or spurs. An appurtenance 120 can include one or more mechanical attachment features on a surface of the appurtenance configured to mate with a surface of the wound dressing 115. The appurtenance 120 can be attached to the wound dressing 115 with a chemical attachment, which can include chemical attachment features such as a pressure-sensitive adhesive, a contact adhesive, or a quick-drying adhesive. An appurtenance 120 can include one or more chemical attachment features on a surface of the appurtenance configured to mate with a surface of the wound dressing 115. The appurtenance 120 is a separate and distinct element that can be attached to the wound dressing 115 in a manner sufficient for operation during the use of a specific wound dressing 115. The appurtenance 120 is a separate and distinct element that can be attached to the wound dressing 115 in an irreversible manner. For example, the appurtenance-wound dressing combination unit, 125, can be disposed of after use. Immediate disposal after use can be desirable to minimize biosafety, contamination and biohazard issues. The appurtenance 120 is a separate and distinct element that can be attached to the wound dressing 115 in a reversible manner. For example, the appurtenance-wound dressing combination unit, 125, can be taken apart into its component wound dressing 115 and appurtenance 120 after use. For example, the appurtenance 120 can be configured for reuse with a new wound dressing 115. The appurtenance 120 can be configured for reuse after treatment, such as after disinfection, cleaning, or sterilization. An appurtenance 120 to a wound dressing 115 can be reused, for example, on a succession of wound dressings 115 used by the same patient.

The appurtenance 120 is configured for functional use only in combination with a wound dressing, such as when attached to the wound dressing 115. The appurtenance 120 is of a size, shape and material for functional use only in combination with a wound dressing, such as when attached to the wound dressing 115. The appurtenance 120 is configured to operate in conjunction with the wound dressing 115. The appurtenance 120 is appended to the wound dressing 115 to generate an appurtenance-wound dressing combination unit 125, as illustrated in the lower right region of FIG. 1. The appurtenance 120 can include at least one region that projects into the structure of the wound dressing 115. In some embodiments, the region that projects into the structure of the wound dressing 115 is of a size and shape to be entirely enclosed within the structure of the wound dressing 115. In some embodiments, the region that projects into the structure of the wound dressing 115 is of a size and shape to project through the wound dressing 115, for example to a region adjacent to a wound. In some embodiments, the region that projects into the structure of the wound dressing 115 is of a size and shape to project through the wound dressing 115, for example to a wound bed region. In some embodiments, the region that projects into the structure of the wound dressing 115 is of a size and shape to project through a portion of the wound dressing 115, for example to a sinus or cavity of the wound bed. In some embodiments, the region that projects into the structure of the wound dressing 115 is of a size and shape to project through a portion of the wound dressing 115, for example to a dressing placed within a sinus or cavity of the wound bed. In some embodiments, the region that projects into the structure of the wound dressing 115 is of a size and shape to project through a portion of the wound dressing 115, for example to a layer placed adjacent to the wound surface. The appurtenance 120 affixed to the wound dressing 115 forms an integrated unit of the appurtenance and the wound dressing as a combination unit 125 (see, e.g. FIGS. 2A, 2B, 3A, 3B, 4, 5, 6 and 8). In some embodiments, the wound dressing-appurtenance combination unit 125 is not readily separable, and the individual wound dressing 115 and appurtenance 120 are not suitable for separation and individual use after they have been joined together. As illustrated in the lower portion of FIG. 1, once the appurtenance 120 is affixed to the wound dressing 115, the appurtenance and the wound dressing together as a combination unit 125 are used to cover and monitor the wound 100.

In some aspects, an appurtenance 120 to a wound dressing 115 is configured to monitor one or more aspects of a wound 100. An appurtenance 120 to a wound dressing 115 can be used by a caregiver or a patient to monitor a wound 100. In some aspects, an appurtenance 120 to a wound dressing 115 is configured to monitor one or more aspects of a wound dressing 115. An appurtenance 120 to a wound dressing 115 can be used by a caregiver, including a patient, to monitor a wound dressing 115. An appurtenance 120 to a wound dressing 115 is configured to allow a user, such as a caregiver or patient, to monitor a wound dressing and the adjacent wound without disturbing the wound dressing 115 such as through removing the dressing 115 from the patient's wound 100. This approach, inter alia, improves comfort to the patient, reduces the chance of accidental infection in or contamination from uncovered wounds, and minimizes time requirements in wound care. In some aspects, an appurtenance 120 to a wound dressing 115 includes a transmitter that sends a signal to a device used by a caregiver or patient to monitor the wound dressing from the same room as the patient. In some aspects, an appurtenance 120 to a wound dressing 115 includes a transmitter that sends a signal to a device used by a caregiver remotely, such as through a pager, remote computing device, cell phone, or dedicated remote signaling device. The signal transmitter sends a signal containing information associated a wound and/or adjacent wound dressing such that a caregiver is able to receive, directly or indirectly, information relating to monitoring a wound and adjacent wound dressing at a distance from the patient, without disturbing the patient and with minimal time spent analyzing the wound 100 or wound dressing 115.

In some aspects, an appurtenance 120 to a wound dressing 115 is part of a system configured to automatically process and save information relating to an appurtenance 120 and the related wound dressing 115 to a medical record system, such as a medical records database. This automatic process reduces the potential for accidental loss or error in data entry regarding wound care, and reduces the time required by a caregiver in data entry into a record.

The wound dressing with the affixed appurtenance combination unit 125 is used to cover the wound 100 on the body part 110. The wound dressing with the affixed appurtenance combination unit 125 can be secured to the body part 110 in a routine manner for the type of wound dressing 115 generally, such as through adhesive integral to the wound dressing 115 or with additional adhesive, wrappings, tapes or glues as generally applicable to the type of wound dressing 115 utilized in a given medical situation. Although not illustrated in FIG. 1, the wound dressing with the affixed appurtenance combination unit 125 can similarly be removed using standard removal procedures, such as with gentle pressure, gentle pulling, unwrapping, allowing it to loosen over time, or biocompatible solvents. The appurtenances 120 described herein can be single-use and disposable along with the affixed wound dressing 115. In some embodiments, the appurtenances 120 described herein can be removed from a first wound dressing and then reconditioned, such as through cleaning or sterilization, and reused with a second wound dressing. In some embodiments, an appurtenance 120 can be reused for multiple wound dressings used on a single wound from a patient. In some embodiments, an appurtenance 120 can be reused after replacement of one or more parts of the appurtenance. The appurtenances 120 described herein are generally intended to be operable for the period of time a given wound dressing 115 is in use under standard conditions and time periods. After a wound dressing with the irreversibly affixed appurtenance combination unit, 125 is removed from the body part 110, it can be disposed of as a unit with routine disposal methods.

It is envisioned that the appurtenances 120 described herein will be utilized while affixed to wound dressings 115 over wounds 100 of a variety of types, and operable to assist in the monitoring of wounds of a variety of types. For example, appurtenances 120 can be used in conjunction with wound dressings 115 to assist in monitoring acute wounds, such as those resulting from accidental injury or surgery. For example, appurtenances 120 can be used in conjunction with wound dressings 115 to assist in monitoring wounds closed by primary intention. For example, the appurtenances 120 can be used to assist in monitoring wound dressings over surgical wounds, such as incisions and surgical stitches. For example, the appurtenances 120 can be used to assist in monitoring wound dressings over acute wounds from injury, such as burn injuries, lacerations, or penetrating wounds. For example, appurtenances 120 can be used in conjunction with wound dressings 115 to assist in monitoring wounds closed by secondary intention. The appurtenances 120 can also be used to assist in monitoring wound dressings over chronic wounds, such as those arising from chronic medical conditions and situations. For example, the appurtenances can be used to monitor the status of wound dressings covering venous leg ulcers, diabetic foot ulcers, pressure ulcers or arterial ulcers. See: "Advances in Wound Healing Techniques," publication D11A, Frost and Sullivan, 2008; "An Overview of Ulceration Wounds," Publication M4BB-54, Frost and Sullivan 2009; and "US Advanced Wound Care Market," Publication N71A-54, Frost and Sullivan 2010, which are each incorporated herein by reference.

The appurtenances 120 described herein can be useful in conjunction with an affixed wound dressing as a combination unit 125 to monitor potential problems with a wound, such as excessive bleeding or other fluid formation that would be present in the wound dressing, or the presence of conditions in the dressing that indicate infection in an adjacent wound. See: Collier, "Recognition and Management of Wound Infections," *World Wide Wounds*, pages 1-9, (January 2004); and Gray, "Assessment, Diagnosis and Treatment of Infection," Wounds UK, vol. 7, no. 2, supplement, (2011), which are each incorporated herein by reference. For example, some types of wound discharge can indicate infection. See, for example, Cutting and Harding, "Criteria for Identifying Wound Infection," *Journal of Wound Care*, vol. 3, no. 4, 198-201 (1994), which is incorporated herein by reference. The appurtenances 120 as part of combination units 125 and related systems described herein can be used in conjunction with readily available types of wound dressings to monitor aspects of the affixed wound dressing, including parameters that indicate that a person should physically examine the wound dressing, such as excessive wetness. The appurtenances 120 as well as related systems described herein can be used in conjunction with readily available types of wound dressings to monitor aspects of the affixed wound dressing, including indications that the wound dressing should be changed (i.e. excessively wet, dry, or soiled). In some embodiments, the appurtenances 120 include additional sensors positioned to detect an aspect of the fluid from the affixed wound dressing, such as the presence of analytes, temperature, or fluid pressure within a conduit or projection.

The appurtenances described herein include transmission units configured to transmit signals, and thereby report information regarding the status of the affixed wound dressing or wound, to associated systems. The resulting information reporting can be used, in some embodiments, to supplement the medical record for a patient in an automated system and automatic process. The resulting information reporting can be used, in some embodiments, to automatically notify a caregiver that the status of the wound dressing has altered, indicating that a person should physically inspect the wound dressing.

As used herein, a caregiver includes at least one of a patient, a caregiver, and medical personnel. A caregiver can utilize some embodiments of the appurtenances and related systems described herein in relation with multiple types of wound dressings. Appurtenances can be fabricated in shapes and sizes to conform to a variety of standard wound dressing sizes, shapes and types. Appurtenances can be fabricated with, for example, transmission units, antennas and sensors appropriate for use with a variety of wound dressings. Appurtenances can be fabricated with, for example, transmission units, antennas and sensors appropriate for different medical situations and monitoring requirements. Appurtenances can be fabricated with, for example, one or more projections of a size, shape and material appropriate for use with a variety of wound dressings. While it is envisioned that every appurtenance will not be appropriate for use with every wound dressing (for example due to size, shape or material compatibility), a given appurtenance is expected to be suitable for use with a range of potential wound dressings. For example, a given appurtenance of a specific size, shape and fabrication, including type of transmission unit, sensors, and projection(s), should be suitable for use with a variety of wound dressings of conforming sizes, shapes and types. Generally, any specific appurtenance embodiment is not expected to only conform to use with a unique wound dressing of a specific size, shape and type. Instead, it is expected that a specific appurtenance embodiment will be suitable for use with a range of wound dressings. Similarly, it is expected that a specific appurtenance embodiment will be suitable for use with a range of wound and wound dressing monitoring requirements.

In the attached drawings, an appurtenance 120 is generally illustrated as affixed to an outer surface of a wound dressing 115, for example an outer surface distal to a surface of the body part 110 adjacent to the wound 100. However, in some embodiments, an appurtenance 120 can be configured to attach to one or more surfaces of a wound dressing 115 adjacent to a surface of the body part 110 adjacent to the wound 100. For example, in embodiments wherein an appurtenance 120 is configured to be attached to a wound dressing 115 of a substantially rectangular, ovoid, or raised conformation, an appurtenance 120 can be configured to be attached to a side surface of the wound dressing 115. For example, in embodiments wherein an appurtenance 120 is configured to be attached to a wound dressing 115 with an unusually strong or thick outer cover layer, the appurtenance 120 can be configured to attach to an underside or interior region of the wound dressing 115. In some embodiments, an appurtenance is configured to attach to a surface of a wound dressing 115 in contact with the surface of the body part 110. In some embodiments, an appurtenance is configured to attach to an internal surface of a wound dressing 115, for example between layers. See FIG. 4.

For example, the appurtenances described herein can be configured to be affixed to a dry gauze dressing, which may or may not include an outer cover layer. For example, the appurtenances described herein can be configured to be attached to a dry silicone or other solid foam dressing, which may or may not include an outer cover layer. For example, the appurtenances described herein can be configured to be affixed to a wound dressing used to close a small or thin wound or surgical incision, such as a butterfly dressing (e.g. SteriStrip™ adhesive strips, available from Nexcare™, part of 3M Corporation). For example, appurtenances such as those described herein can be configured to be affixed to a dressing configured to maintain moisture or other materials adjacent to the wound surface. For example, appurtenances such as those described herein can be configured to be used with hydrogel wound dressings, for example Aquaflo™ Hydrogel Wound Dressing by Kendall Corporation, or Elasto-Gel™ Hydrogel Occlusive Dressing by Southwest Technologies. For example, appurtenances such as those described herein can be affixed to wound dressings including hydrocolloids, for example DuoDERM CGF Sterile Hydrocolloid Dressing manufactured by DuoDERM Corporation. For example, appurtenances such as those described herein can be configured to be used with wound dressings containing one or more medicinal agents, such as antibiotics. For example, appurtenances such as those described herein can be used with wound dressings impregnated with PHMB (Polyhexamethylene Biguanide), such as Telfa™ A.M.D. antimicrobial wound dressings, manufactured by Kendall Corporation. For example, appurtenances such as those described herein can be configured to be used with wound dressings including ionic silver, such as Maxorb™ Extra Ag wound dressings manufactured by Medline Corporation. Appurtenances such as those described herein can be configured to be affixed to wound dressings over wounds wherein the tissue of the wound is being directly monitored using other devices, for example as described in U.S. Pat. No. 6,963,772 to Bloom et al., titled "User-retainable Temperature and Impedance Monitoring Methods and Devices," which is incorporated herein by reference. Appurtenances such as those described herein can be configured to be affixed to wound dressings over wounds wherein the patient is being directly monitored using other devices, for example as described in U.S. Pat. No. 7,030,764 to Smith and Cooper, titled "Apparatus and Method for Reducing the Risk of Decubitus Ulcers;" U.S. Pat. No. 7,297,112 to Zhou et al., titled "Embedded Bio-Sensor System;" U.S. Pat. Nos. 7,372,780, 8,014,234 and 7,813,226 to Braunberger, titled "Timing System and Device and Method for Making the Same;" U.S. Pat. No. 7,666,151 to Sullivan et al., titled "Devices and Methods for Passive Patient Monitoring;" U.S. Pat. No. 7,703,334 to Cochran, titled "Bandage Type Sensor Arrangement and Carrier Assembly Therefore, and Method of Manufacture;" and International Patent Publication No. WO 2005/009328 to Nikolic, titled "ABT-Anti-Bedsore Timer," which are each incorporated herein by reference. Appurtenances such as those described herein can also be used in conjunction with a system to monitor assets within a health care facility, for example as described in US Patent Application No. 2007/0247316 to Wildman et al., titled "Article Locating and Tracking Apparatus and Method," which is incorporated herein by reference.

Wound dressings 115 such as those described herein are generally used for a relatively short period of time, on the order of hours or days, and then removed for disposal. Similarly, a wound dressing with an affixed appurtenance combination unit 125 should be configured for use over the course of hours or days and then removed and disposed of using standard methods. A wound dressing with an affixed appurtenance can be configured for single use and to be disposable after use. For example, a caregiver can require a new wound dressing every 24 hours (1 day) for an acute wound. Any wound dressing utilized in this type of situation would, consequently, be of a size, weight and shape to remain affixed to the wound region over the course of at least a 24 hour period and then removed for disposal. An appurtenance to a wound dressing intended for use over the course of a 24 hour time period, similarly should be of a size, shape, material fabrication, and capabilities to function while affixed to the wound dressing over the 24 hour period that the dressing is in use. An appurtenance to a wound dressing can be configured to be lightweight and of a low form factor to minimize disruption to the wound dressing. For example, an appurtenance can be configured to weigh less than approximately 30 grams, or less than approximately 40 grams, or less than approximately 50 grams. As an additional example, a caregiver can decide that for another type of wound, such as a chronic wound, the wound dressing needs to be removed and replaced once every 2 days, every 3 days, or every 4 days, or every 5 days, or every 6 days, or every 7 days. Correspondingly, an appurtenance affixed to a wound dressing intended for use over the course of at least 2 to 7 days should be of a size, shape, material fabrication, and capabilities to function while affixed to the wound dressing over at least the 2 to 7 day period that the dressing is in use. In embodiments wherein an appurtenance is intended for reuse, such as reuse on a second or subsequent wound dressing used over a wound, the appurtenance should be of a size, shape, material fabrication and capabilities to function during the entire intended use, including the time period of removal from a first wound dressing and application to a second wound dressing.

FIGS. 2A and 2B depict further aspects of some embodiments of appurtenances to wound dressings. FIGS. 2A and 2B depict cross-section views of an appurtenance 120 to a wound dressing 115. As illustrated in FIG. 2A, the appurtenance 120 includes a substantially planar section and a projection 200. The substantially planar section includes a surface 230 configured to substantially conform with an outer surface of the wound dressing 115. In some embodiments, the surface 230 of the appurtenance 120 configured to conform with an outer surface of the wound dressing 115 can include adhesive of a type expected to irreversibly adhere to the surface of the wound dressing 115. In some embodiments, the surface 230 of the appurtenance 120 configured to conform with an outer surface of the wound dressing 115 can include adhesive of a type expected to adhere to the surface of the wound dressing 115 for a period of time, and to be removable. In some embodiments, the surface 230 of the appurtenance 120 configured to conform with an outer surface of the wound dressing 115 can include barbs, hooks, pins, prongs or other extensions configured to adhere or fix onto the outer surface of the wound dressing 115. For example, an appurtenance 120 configured to conform with an outer surface of the wound dressing 115 can include barbs, hooks, pins, prongs or other extensions that irreversibly adhere to the outer surface of the wound dressing 115, such as by imbedding into the outer surface. For example, an appurtenance 120 configured to conform with an outer surface of the wound dressing 115 can include barbs, hooks, pins, prongs or other extensions that reversibly adhere to the outer surface of the wound dressing 115, such as by reversibly interacting with extensions projecting from the outer surface.

The appurtenance 120 depicted in FIGS. 2A and 2B includes a projection 200. As shown in FIGS. 2A and 2B, the projection extends from a surface 230 of the appurtenance 120 configured to conform with an outer surface of the wound dressing 115. The single projection depicted in FIGS. 2A and 2B projects at an angle from the plane formed by the substantially planar section of the appurtenance 120 conforming to the surface of the wound dressing 115. This angle is depicted in FIG. 2A as $\theta$. In FIGS. 2A and 2B, for example, the angle shown as $\theta$ is approximately 135 degrees. However, as will be more evident from further description below (see, e.g. in relation to FIG. 12), in some embodiments an appurtenance 120 can include a plurality of projections 200. Depending on the embodiment, the projections 200 can also be at a variety of angles relative to the section of the appurtenance 120 conforming to the surface of the wound dressing 115. For example, in some embodiments, one or more projections can be at angles less than approximately 135 degrees, between approximately 135 degrees and approximately 90 degrees, or substantially at approximately 90 degree angles relative to a planar section of the appurtenance 120. In some embodiments, an appurtenance 120 includes a substantially planar region including a transmission unit, wherein the substantially planar region is configured to conform with an outer surface of the wound dressing 115, and one or more projections 200 projecting substantially perpendicular to the surface 230 configured to conform with an outer surface of the wound dressing 115. Depending on the embodiment, the projections 200 can project in a direction substantially away from the surface of the appurtenance configured to conform with an outer surface of the wound dressing 115 (e.g. as in FIGS. 2A and 2B), or angle in a direction substantially perpendicular to the surface 230 configured to conform with an outer surface of the wound dressing 115 of the appurtenance. Some embodiments include at least one projection 200 which is curvilinear. Some embodiments include at least one projection 200 which is a composite shape. In embodiments including one or more projections that are not substantially straight, an angle (e.g. $\theta$ as illustrated in FIG. 2A) of the projection 200 can be determined by the angle formed at the base of the projection immediately adjacent to the surface of the appurtenance configured to conform with an outer surface of the wound dressing 115.

The projection 200 can be a substantially hollow tubular structure. Although not illustrated in FIGS. 2A and 2B in this view, a substantially hollow tubular structure of the projection 200 includes an opening on the distal end of the projection 200. While the projection 200 depicted in FIGS. 2A and 2B can be a substantially tubular structure, in some embodiments projections can be of different shapes and conformations. For example, a projection 200 can be solid, tubular, conical, cylindrical, tapered, curved, angular or other shape or combination of shapes as appropriate to the specific embodiment. Embodiments including a plurality of projections can include projections of different sizes and shapes. A projection 120 can be substantially straight and form a substantially linear internal channel (e.g. as depicted in FIGS. 2A, 2B, 8 and 9), or it can be curved and form a substantially curvilinear internal channel. The drawings illustrated herein are not to scale. The drawings illustrated herein represent relationships and shapes of the items described. Although not expressly illustrated herein, a projection 200 can be relatively large relative to the total size of the appurtenance. For example, the volume of a projection or a group of projections attached to an appurtenance can be 51%, 55%, 60%, 65%, 70%, 75%, 80%, 85%, 90%, 95% or 100% of the volume of the portion of the appurtenance configured to conform with an outer surface of a wound dressing (e.g. the substantially planar region as illustrated in FIGS. 2A and 2B). Similarly, a projection 200 can be relatively small relative to the total size of the appurtenance. For example, the volume of a projection or a group of projections attached to an appurtenance can be 49%, 45%, 40%, 35%, 30%, 25%, 20%, 15%, 10%, or 5% of the volume of the portion of the appurtenance configured to conform with an outer surface of a wound dressing (e.g. the substantially planar region as illustrated in FIGS. 2A and 2B). In some embodiments, a projection 200 is located at an edge region of the substantially planar region of the appurtenance 120, and in some embodiments a projection 200 is located substantially centrally to the planar surface 230 of the appurtenance 120 configured to conform with an outer surface of the wound dressing 115. In some embodiments, a substantially planar appurtenance 120 includes at least one projection 200 wherein the entire appurtenance 120 is of a size and shape to be secured against an external surface of a wound dressing 115 with force, for example from a human thumb or finger.

In some embodiments, an appurtenance 120 can be fabricated with one or more regions configured for the attachment of different modules. In some embodiments, an appurtenance 120 includes modules that are configured for removal and replacement. In some embodiments, an appurtenance 120 includes modules that are configured to improve efficiency in fabrication of the appurtenance 120. During fabrication, a basic appurtenance structure can be utilized and different specific modules added as desired in a particular embodiment. For example, an appurtenance 120 can be fabricated with at least one region configured to attach a projection. For example, a region configured to attach a projection can include a region with a surface conforming to an outer surface of the projection. For example, a region configured to attach a projection can include a conduit configured to align with the hollow interior of the projection. The region of the appurtenance 120 configured to attach a projection can be configured for attachment of different projection types, depending on the embodiment. For example, the region of the appurtenance 120 configured to attach a projection can be configured for attachment of projections of different lengths or different materials as desired in the construction of a particular embodiment. In some embodiments, an appurtenance 120 can have multiple regions configured for attachment of multiple projections of different types. In some embodiments, an appurtenance 120 can have one or more removable antenna modules. For example, an appurtenance 120 can have one or more removable transmission units, such as radio frequency identification (RFID) units. In some embodiments, a module can include a spacer element, or a component configured to assist in physically positioning one or more other modules.

An appurtenance 120 can be fabricated from a variety of materials, as appropriate to an embodiment. An appurtenance 120 can be fabricated, for example, substantially from a plastic material. For example, a structural portion, such as a shell or base can be fabricated from a plastic material. For example, one or more projections can be fabricated from a plastic material. An appurtenance 120 can be fabricated, for example, from one or more acrylics, polyesters, silicones, polyurethanes and halogenated plastics. An appurtenance 120 can include one or more projections 200 fabricated, for example, from one or more plastic materials. An appurtenance 120 can include one or more projections 200 fabricated, for example, from one or more acrylics, polyesters, silicones, polyurethanes and halogenated plastics. An appurtenance 120 can be fabricated from one or more bio-compatible materials, for example bio-compatible plastics, resins, epoxies and metals. An appurtenance 120 can be fabricated from one or more composite materials, such as plastic with an overlay of epoxy or plastic with an overlay of one or more metals. An appurtenance 120 including a transmission unit can include, for example, one or more metal components, for example as circuitry or as one or more antennas. An appurtenance 120 including a transmission unit can include, for example, stainless steel, copper or zinc alloy. An appurtenance 120 can be fabricated from one or more ceramic materials, such as within a transmission unit. Generally, it is envisioned that materials with low weight will be suitable for a variety of appurtenance embodiments, so as to reduce weight and associated physical stress on a wound dressing. Similarly, it is envisioned that materials with sufficient strength and toughness to be fabricated into small and thin components will be desirable for fabrication of appurtenance embodiments. As the appurtenances are to be permanently affixed to the wound dressings and disposed of with the wound dressings, materials that do not require special handling or disposal are preferable in most embodiments.

In some embodiments, the appurtenance 120 includes a substrate, (e.g. 250) that is configured to attach to the wound dressing 115. For example, the substrate can be configured as a support for other features of the appurtenance 120. For example, the substrate can stabilize other features of the appurtenance 120 in their relative positions. For example, the substrate can cover and protect other features of the appurtenance 120. In some embodiments, the substrate includes a substantially planar structure wherein the area of surface 230 is less than the area of the wound dressing 115 (see, e.g. FIG. 5). In some embodiments, the substrate is configured to irreversibly attach directly to an external surface of the wound dressing 115. In some embodiments, the substrate is configured to chemically attach to the wound dressing 115. In some embodiments, the substrate includes an adhesive on a surface conforming to an external surface of the wound dressing 115 (e.g. surface 230 in FIG. 2A). For example, the surface conforming to an external surface of the wound dressing 115 can include a glue, epoxy, sealant, mucilage, paste or other binder material. In some embodiments, the surface of the substrate conforming to an external surface of the wound dressing 115 can include an adhesive covered by a removable protective sheet configured for detachment and exposure of the adhesive when the appurtenance 120 is attached to the wound dressing 115. In some embodiments, the substrate is configured to mechanically attach to the wound dressing 115. In some embodiments, the surface 230 of the substrate of the appurtenance 120 configured to conform with an outer surface of the wound dressing 115 can include barbs, hooks, pins, prongs or other extensions configured to adhere or fix into the outer surface of the wound dressing 115. In some embodiments, the substrate is configured to integrate within the wound dressing 115 (see, e.g. FIG. 4). In some embodiments, the substrate is configured to attach to an outer surface of the wound dressing 115. In some embodiments, the surface 230 of the substrate of the appurtenance 120 configured to conform with a surface of the wound dressing 115 can include a mixture or combination of any of the above.

In some embodiments, the substrate includes a flexible material. For example, the substrate can include a pliable plastic, a woven fabric material, soft mesh or other flexible material. In some embodiments, the substrate includes a rigid material. For example, the substrate can include at least one rigid plastic material in a location configured to provide support for a portion of the appurtenance. For example, the substrate can include at least one rigid plastic material at a location configured to attach a projection, the rigid plastic configured to provide physical support for the attached projection. In some embodiments, the substrate includes at least one bio-compatible material. For example, the substrate can include one or more bio-compatible plastic materials, one or more bio-compatible fabric materials, or one or more bio-compatible metals.

FIG. 2A depicts a cross section view of an appurtenance 120 adjacent to a wound dressing 115. As shown in FIG. 2A, the wound dressing 115 includes a dressing layer 220 and an outer layer 210. Not all wound dressings 115 should be expected to include multiple layers, and it is to be expected that some wound dressings 115 substantially include only a wound dressing material and not additional layers, structures or coverings. However, as illustrated in FIGS. 2A and 2B, in some embodiments wound dressings 115 include a plurality of layers. For example, a wound dressing 115 can include one or more outer layers 210 configured to protect and isolate the wound dressing layer(s) from microbes, external dirt and debris, dryness, wetness or other external factors. An outer layer can be fabricated from materials such as firm plastics or mesh materials. An outer layer can include a surface larger than the surface of the wound dressing layer, and can include adhesives on that surface configured to adhere the entire wound dressing to a body surface. A wound dressing 115 can include one or more layers of wound dressing 220 materials, such as gauze, films, foams, or sponges. A wound dressing 115 can include one or more layers of hydrogels, colloid gels, and medicinal agents impregnated within one or more layers of the wound dressing 220 or on a surface of the wound dressing 220 configured to face a wound.

A surface 230 of an appurtenance 120 can be configured to conform to the surface of the outer layer 210 of a wound dressing 115. For example, the surface can be of a size and shape that substantially conforms with the surface of the wound dressing 115. A surface 230 of an appurtenance 120 can include barbs, hooks, pins, prongs or other extensions configured to reversibly or irreversibly stick into the outer surface of the wound dressing 115. A surface 230 of an appurtenance 120 can include one or more adhesives of a type to attach the appurtenance 120 to the wound dressing 115.

FIG. 2B illustrates the appurtenance 120 and the wound dressing 115 of FIG. 2A after the appurtenance 120 is affixed to the wound dressing 125. As illustrated in FIG. 2B, a projection 200 of an appurtenance 120 can be configured to pierce through the outer layer 210 and into a wound dressing layer 220. A projection 200 of an appurtenance 120 can be of a size and shape to project from the outer surface of the wound dressing 115 to within layers of the wound dressing 115. A projection 200 can be of a size and shape to extend into an interior region of the wound dressing 115. A projection 200 can be of a size and shape to project within an interior region of the wound dressing 115. As shown in FIG. 2B, a projection 200 can be of a size and shape to project underneath one or more superficial structures of the wound dressing 115 (such as an outer layer 210) when the wound dressing 115 is in use. A projection 100 can be of a size and shape to project through a width of the wound dressing 115 when the appurtenance 120 is attached to the wound dressing 125. Also as illustrated in FIG. 2B, a projection 200 extending within the layers of the wound dressing 125 can be positioned so that fluids, (depicted as dotted arrows), can enter a hollow within the projection 200 through capillary action.

FIG. 2B also illustrates that in some embodiments a cover 240 is attached to the surface of the appurtenance 120 as well as to the surface of the wound dressing, such as to an outer layer of the wound dressing 210. An appurtenance 120 can include a substantially planar cover, the cover including an adhesive on a surface conforming to a surface of a wound dressing, the substantially planar cover configured to cover a location where the projection extends into the wound dressing. A cover 240 can be fabricated, for example, from a flexible plastic or mesh material. A cover 240 can be fabricated, for example, from an inflexible plastic or mesh material and configured in a size and shape to conform with the surfaces of the appurtenance 120 as well as to the surface of the wound dressing 115. A cover 240 can include adhesive on a surface facing the appurtenance and the wound dressing, the adhesive configured to attach the cover to the appurtenance and to the wound dressing. A cover 240 can be configured to stabilize the position of the appurtenance 120 relative to the wound dressing 115 when the appurtenance is affixed to the wound dressing 125 (e.g. as in FIG. 2B). A cover 240 can be configured to secure the appurtenance 120 relative to the wound dressing 115 when the appurtenance is affixed to the wound dressing 125 (e.g. as in FIG. 2B). A cover 240 can be configured to seal the juncture between the appurtenance 120 and the wound dressing 115, for example from dirt, debris, wetness or microbes that can enter the interior of the wound dressing if the juncture is not sealed. A cover 240 can be configured to seal any potential gaps between the projection 200 of the appurtenance 120 and the wound dressing 115, for example to seal any potential gaps from dirt, debris, external wetness or microbes that can enter the interior of the wound dressing if the gap is not sealed.

In some embodiments, an appurtenance 120 to a wound dressing 115 is substantially sterilized prior to use. For example, the appurtenance 120 can be treated with one or more chemical disinfectants or UV surface radiation for a period of time sufficient to substantially sterilize the appurtenance 120 prior to use. For example, the appurtenance 120 can be treated with one or more antimicrobial gasses, for example ethylene oxide (ETO), prior to use. For example, the appurtenance 120 can be treated with a chemical sterilizing agent, such as hydrogen peroxide in liquid or vapor form, prior to use. For example, the appurtenance 120 can be treated with steam as an anti-infective prior to use. For example, the appurtenance 120 can be irradiated prior to use, such as with gamma rays, electron beams, ultraviolet rays, or X-rays. In some embodiments, an appurtenance 120 to a wound dressing 115 includes a sterile wrapper. For example, an appurtenance 120 to a wound dressing 115 can be stored and/or transported within a sterile wrapper, such as a firm paper wrapper or a plastic film. A sterile wrapper configured for storage and/or transport of an appurtenance can be treated to minimize contamination, for example coated with one or more anti-microbial agents.

Figure 3A:
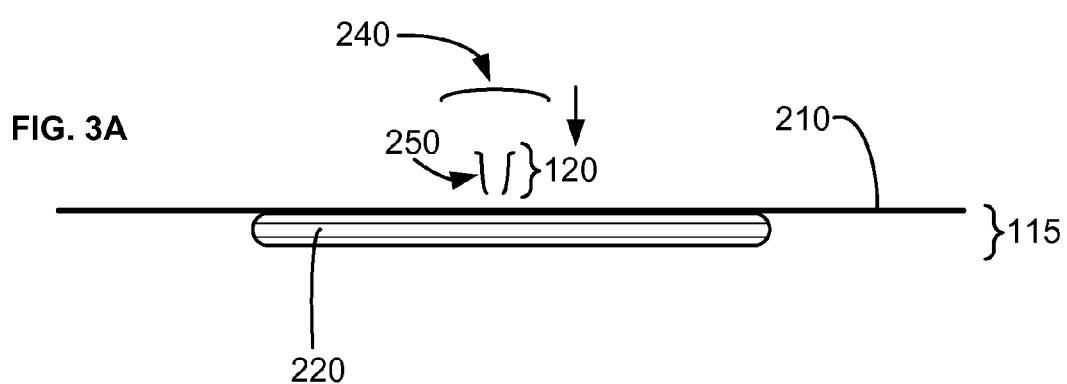
FIG. 3A is a schematic of an appurtenance to a wound dressing prior to attachment to a wound dressing.
Figure 3B:
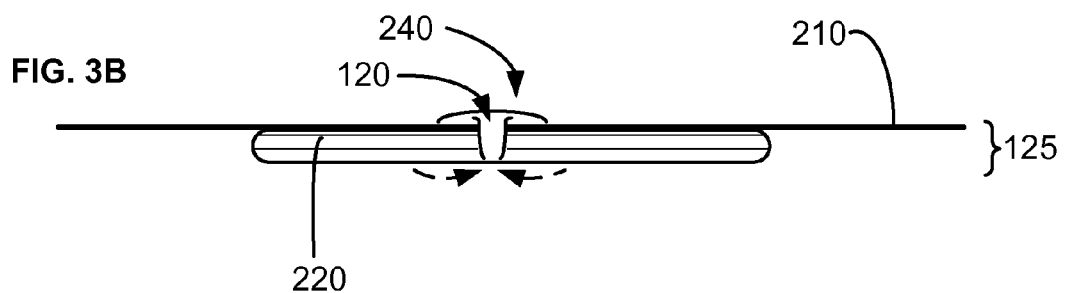
FIG. 3B is a schematic of an appurtenance to a wound dressing after attachment to a wound dressing.

FIGS. 3A and 3B illustrate aspects of some embodiments of an appurtenance 120 to a wound dressing 115 in a cross-sectional view. In some embodiments, an appurtenance 120 includes an enclosure of a height and width to fit substantially within an interior region of a wound dressing 115. FIG. 3A depicts an appurtenance 120 of a size and shape to substantially penetrate an outer cover 210 and into a dressing region 220 of a wound dressing 115. The appurtenance 120 depicted in FIGS. 3A and 3B is a cross section view of a substantially conical shape with an opening at the lower region of the cone (downward in FIGS. 3A and 3B). The main structure of the appurtenance is depicted as 250. As illustrated in FIG. 3A and FIG. 3B, some embodiments include a cover 240. A cover 240 can be of a size and shape to seal the surface of the appurtenance 120 exposed at the surface of the wound dressing. FIG. 3B depicts the appurtenance 120 affixed to the wound dressing 125. The appurtenance 120 depicted in FIG. 3B projects through the outer layer 210 of the wound dressing and into the interior wound dressing layer 220. Also as illustrated in FIG. 3B, an appurtenance 120 extending within the layers of the wound dressing 125 can be positioned so that fluids, depicted as dotted arrows, can enter an opening or aperture in the appurtenance 120 through capillary action. See also FIG. 7.

Figure 4:
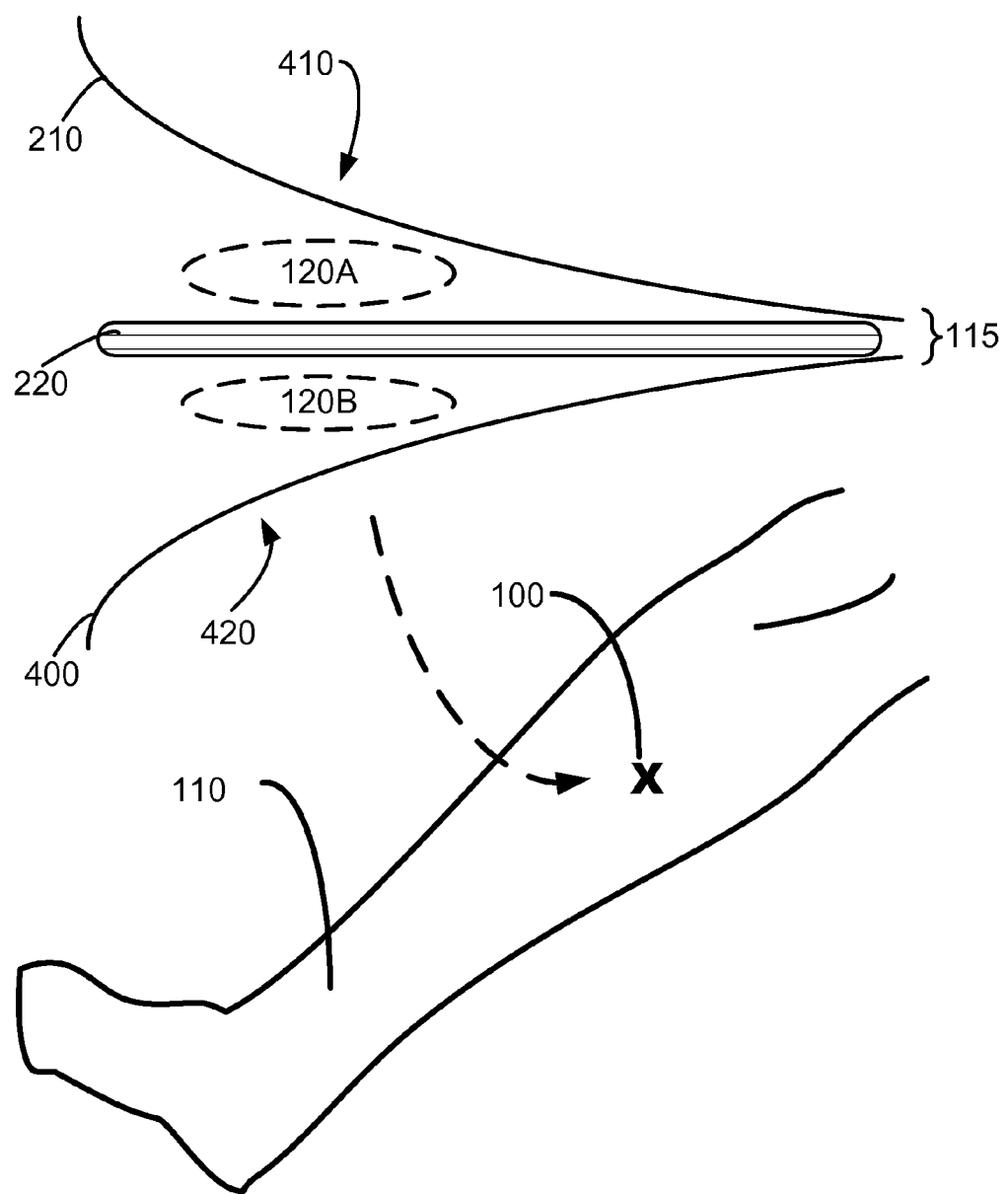
FIG. 4 is a schematic of layers of a wound dressing and potential placement of appurtenances relative to the layers.

FIG. 4 depicts aspects of a wound dressing 115 and some potential positions of an appurtenance 120A, 120B relative to the wound dressing 115. As shown in FIG. 4, a wound dressing 115 can include an outer layer 210, a dressing layer 220 and a wound contact layer 400. For example, the outer layer 210 can include a plastic film or mesh configured to protect the external surface of the wound dressing 115. The outer layer 210 can include at least one exterior surface 410 positioned away from the wound 100 when the wound dressing 115 is in use. For example, the dressing layer 220 can include one or more layers of gauze or absorbent material. For example, the dressing layer 220 can include a hydrogel. For example, the dressing layer 220 can include one or more layers of foam dressing. For example, the wound contact layer 400 can include a plastic mesh film configured to reduce chafing or adherence of the wound dressing 115 to the wound 100. For example, the wound contact layer 400 can include a surface 420 configured to substantially conform with an outer surface of the wound 100. For example, the wound contact layer 400 can include a surface 420 configured as a non-planar surface to substantially conform with an outer surface of the wound 100. For example, the wound contact layer 400 can include a surface 420 including a flexible material expected to substantially conform with an outer surface of the wound 100, such as a soft foam or gel material. As shown in FIG. 4, some embodiments of the appurtenances 120A, 120B described herein are configured to be positioned within the layers of a wound dressing 115. As shown in FIG. 4, an appurtenance 120 A can be positioned between an outer layer 210 and a dressing layer 220 of a wound dressing 115. Also as shown in FIG. 4, an appurtenance 120 A can be positioned between a dressing layer 220 and a wound contact layer 400 of a wound dressing 115. During use, the wound dressing 115 is condensed so that all of the layers 210, 220, 400 are positioned adjacent to each other and also to any appurtenance 120 A, 120 B placed between the layers 210, 220, 400. The wound dressing 115 with attached appurtenance 120 A, 120 B is then reversibly affixed to the surface of a body part 110 and covering a wound 100.

Figure 5:
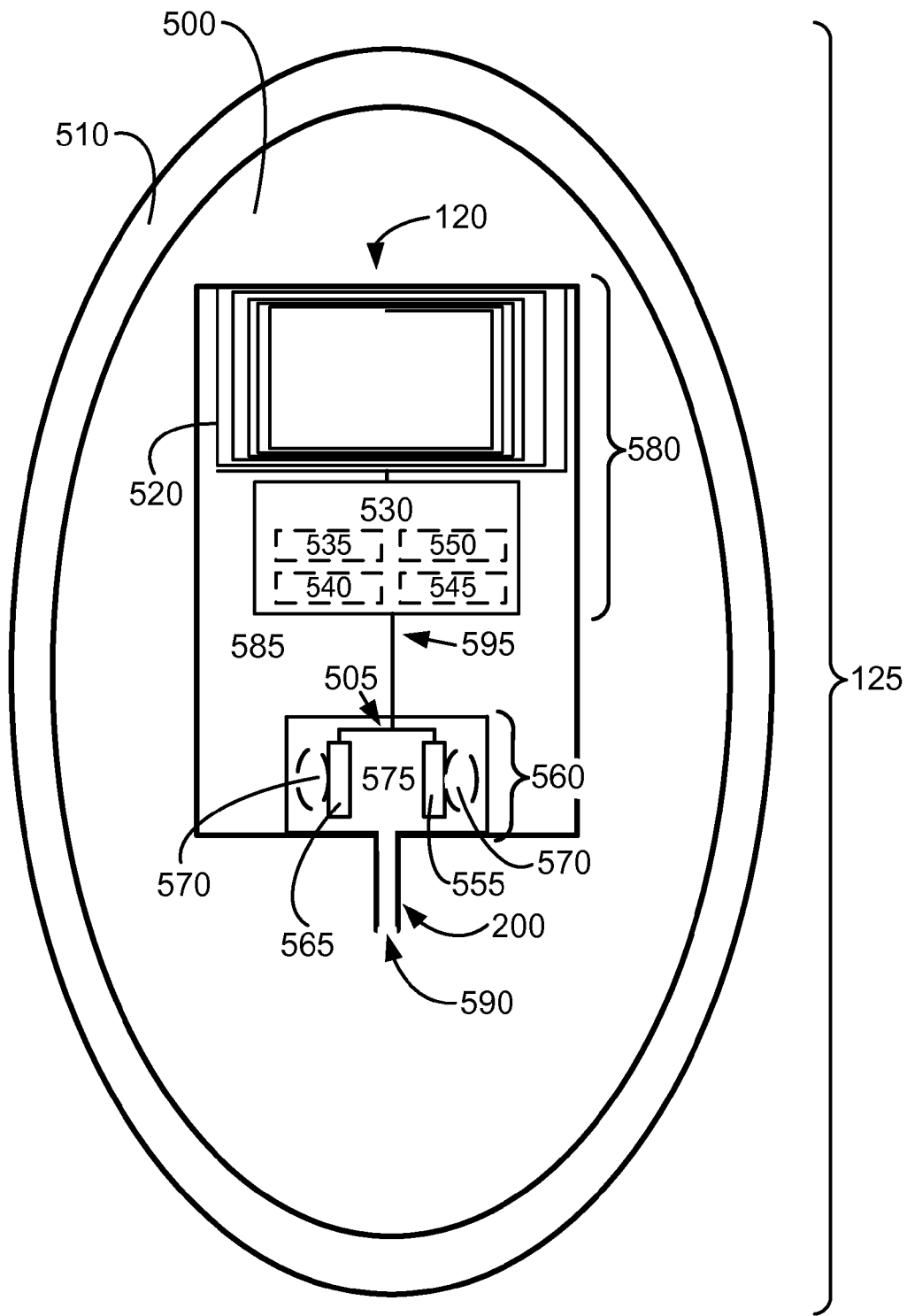
FIG. 5 is a schematic of an appurtenance to a wound dressing.

FIG. 5 illustrates aspects of an appurtenance 120 affixed to a wound dressing unit 125. The view illustrated in FIG. 5 is a substantially top-down view, as seen from the top of an appurtenance affixed to a wound dressing unit 125 looking down on to the unit. The side of the wound dressing-appurtenance combination unit 125 illustrated in FIG. 5 is the side that would be away from a wound during use (e.g. surface 410 as shown in FIG. 4). The side of the wound dressing-appurtenance combination unit 125 illustrated in FIG. 5 is the distal face to the surface of the unit configured for use adjacent to a body part. As shown in FIG. 5, a wound dressing can include a wound covering region 500 and an edge region 510. The wound covering region 500 can include one or more layers of a wound dressing, such as gauze, foam, hydrocolloids, and other types of wound dressings singly or in combination. The edge region 510 can include, for example, a structural region configured to provide shape and support to the wound covering region 500. The edge region 510 can include, for example, an adhesive configured to attach the edge region 510 to a surface of a body part in an area adjacent to a wound. The edge region 510 can include, for example, a cover configured to seal the edge region 510 and the adjacent body part surface from substances moving between the edge region 510 and the adjacent body part surface. For example, the edge region 510 can include a cover configured to prevent wetness, debris, dirt or microbial agents from travelling between the edge region 510 and the body surface.

FIG. 5 illustrates an appurtenance 120 affixed to a wound dressing to form a wound dressing-appurtenance combination unit 125. The appurtenance 120 includes a substrate 585 configured to attach to the wound dressing 500, 510. The appurtenance 120 includes a fluid-activated voltaic cell 560 attached to the substrate 585. The appurtenance 120 includes a transmission unit 580 attached to a surface of the substrate 585, the transmission unit 580 including circuitry 530 and an antenna 520. The transmission unit 580 is configured to transmit a signal in response to current generated by the fluid-activated voltaic cell 560. The fluid-activated voltaic cell 560 is electrically connected to the transmission unit 580 with a wire connector 595. The appurtenance 120 includes a projection 200 operably attached to the fluid-activated voltaic cell 560. The projection 200 is of a size and shape to extend into an interior region of the wound dressing 500, 510 (not depicted in FIG. 5 for purposes of illustration of the structure of the appurtenance 120, but see FIG. 2B). The projection 200 is configured to sample a fluid within an interior region of the wound dressing 500, 510. For example, the projection 200 includes an opening 590 at the end of the projection 200 distal to the end of the projection 200 adjacent to the substrate 585, the opening 590 configured to allow fluid flow from an interior region of the wound dressing 500, 510 into the interior region 575 of the fluid-activated voltaic cell 560.

As shown in FIG. 5, an appurtenance 120 affixed to a wound dressing to form a wound dressing—appurtenance combination unit 125 includes a substrate 585. The substrate 585 can include, for example, a flexible plastic, which can be configured in a thin film or as a mesh of no more than a few millimeters (mm) in thickness. For example, the substrate 585 can be no more than 3 mm, or no more than 5 mm, thick depending on the embodiment. The substrate 585 can include, for example, a flexible paper material. The substrate 585 can include, for example, a composite material. The substrate 585 can include, for example, one or more materials with properties such as durability, strength, cost, weight, biocompatibility and disposability that are suitable for a given embodiment. As illustrated in FIG. 5, the substrate 585 is configured to irreversibly attach to the wound covering region 500 of the wound dressing. For example, the substrate 585 can include an adhesive material on a face configured to conform to a surface of the wound dressing 500. For example, the substrate 585 can include one or more barbs, hooks or other projections on the face configured to conform to the surface of the wound dressing 500.

FIG. 5 depicts a fluid-activated voltaic cell 560 attached to the substrate 585. As described herein, a "fluid-activated voltaic cell" is an electrochemical cell that is configured to derive electrical energy from a spontaneous oxidation-reduction (redox) reaction that takes place within the cell when fluid is present within the cell. A fluid-activated voltaic cell includes at least two electrodes joined by an electrical connector. The electrodes are located within an interior region of the fluid-activated voltaic cell. The electrodes are positioned with a space or a gap between the electrodes. When fluid from a wound dressing is present in the space, one electrode will be reduced and the other will be oxidized by contact with the fluid, which serves as an electrolyte. As shown in FIG. 5, the fluid-activated voltaic cell 560 includes a first electrode 555 and a second electrode 565 separated by space in an interior region 575. A first electrode 555 and a second electrode 565 are fabricated from materials with different electrochemical properties, particularly different oxidation-reduction potentials. The materials fabricating the electrodes can be selected for their oxidation-reduction potentials in the presence of fluid. The materials fabricating two or more electrodes can be selected for their oxidation-reduction potentials in combination. For example, a first electrode can be fabricated from copper and a second electrode can be fabricated from lead. For example, a first electrode can be fabricated from zinc and a second electrode can be fabricated from copper. For example, a first electrode can be fabricated from copper and a second electrode can be fabricated from iron. For example, a first electrode can be fabricated from zinc and a second electrode can be fabricated from lead. For example, a first electrode can be fabricated from zinc and a second electrode can be fabricated from nickel. It has been estimated that electrochemical cells including different combinations of electrodes can produce voltages of approximately 0.5 V to approximately 1.7 V. See: Goodisman, "Observations on Lemon Cells," Journal of Chemical Education, vol. 78, no. 4, 516-518 (2001); Lee et al., "Water Activated Disposable and Long Shelf Life Microbatteries," 16th IEEE Micro Electro Mechanical Systems Conference, Kyoto, 19-23 Jan. 2003; and Sammoura et al., "Water Activated Disposable and Long Shelf Life Microbatteries," Sensors and Actuators A 111:79-

86 (2004), which are each incorporated by reference herein. As shown in FIG. 5, the interior region 575 of the fluid-activated voltaic cell 560 is positioned between the first electrode 555 and the second electrode 565 and configured to include a space within the interior region 575 that can be occupied by fluid flow from the wound dressing. An electrical connector 505, such as a wire, joins to the first electrode 555 and the second electrode 565. In some embodiments, the fluid-activated voltaic cell 560 can include an anode and a cathode. The first electrode 555 and the second electrode 565 are positioned with the interior region 575 between them and configured so that fluid from the wound dressing can flow into the interior region 575.

Some embodiments include at least one enhancement unit 570 positioned adjacent to one or both of the first and second electrodes 555, 565 within the fluid-activated voltaic cell 560. An "enhancement unit" includes at least one chemical enhancer of the spontaneous redox reaction that takes place within the cell when fluid is present within the cell. The chemical enhancer promotes an electrochemical reaction within the fluid-activated voltaic cell 560. The chemical enhancer of the voltaic cell is configured to be released when it contacts the fluid from the wound dressing, such as wound-related liquids, including blood and pus. In some embodiments, the enhancement unit includes at least one dry acid unit configured to release acid when contacted by a liquid. For example, the enhancement unit can include a dry or crystalline form of an acid, such as citric acid or ascorbic acid.

Some embodiments include at least one desiccant unit within the fluid-activated voltaic cell 560. A "desiccant unit" includes one or more desiccant agents packaged as appropriate for the agent and embodiment. For example, at least one desiccant unit can be configured to reduce humidity within the interior region 575 of the fluid-activated voltaic cell 560. In some embodiments, at least one desiccant unit can be configured to form a region of low humidity within the interior region 575 of the fluid-activated voltaic cell 560. In some embodiments, at least one desiccant unit can be configured to encourage fluid flow into a region of low humidity within the interior region 575 of the fluid-activated voltaic cell 560 from a region of higher humidity, such as the interior of a moist wound dressing. In some embodiments, at least one desiccant unit can be configured to maintain a region of low humidity within the interior region 575 of the fluid-activated voltaic cell 560 during transport or storage of the appurtenance. For example, the at least one desiccant unit can be configured to maintain relatively low humidity within at least one enhancement unit 570 positioned adjacent to one or both of the first and second electrodes 555, 565 within the fluid-activated voltaic cell 560 prior to use of the appurtenance. A desiccant unit can be configured to produce a humidity gradient between a relatively humid interior of a moist wound dressing and a relatively dry interior region 575 of the fluid-activated voltaic cell 560. Such a humidity gradient can encourage fluid flow into the fluid-activated voltaic cell 560 when sufficient fluid is present within the attached wound dressing.

Some embodiments include at least one humectant unit within the fluid-activated voltaic cell 560. A "humectant unit" includes one or more desiccant agents packaged as appropriate for the agent and embodiment. In some embodiments, at least one humectant unit can be configured to encourage fluid flow into a region of low humidity within the interior region 575 of the fluid-activated voltaic cell 560 from a region of higher humidity, such as the interior of a moist wound dressing. A humectant unit can be configured to produce a humidity gradient between the interior of a moist wound dressing and the interior region 575 of the fluid-activated voltaic cell 560. Such a humidity gradient can encourage fluid flow into the fluid-activated voltaic cell 560 when sufficient fluid is present within the attached wound dressing.

Also as illustrated in FIG. 5, the appurtenance 120 affixed to a wound dressing to form a wound dressing-appurtenance combination unit 125 includes a transmission unit 580 attached to a surface of the substrate. The transmission unit 580 includes circuitry 530 and at least one antenna 520. Although the transmission unit 580 is illustrated as visible in FIG. 5, in some embodiments all or part of the transmission unit 580 will be covered and not be visible. For example, the transmission unit 580 may be under a cover (e.g. 240 as illustrated in FIGS. 2A, 2B, 3A and 3B).

The transmission unit 580 is configured to transmit a signal in response to power generated by the fluid-activated voltaic cell 560. The transmission unit 580 is configured to transmit a signal utilizing the power generated by the fluid-activated voltaic cell 560. The transmission unit 580 can be configured to respond to activation of the fluid-activated voltaic cell 560. The transmission unit 580 can be configured to transmit a signal in response to a current generated by the fluid-activated voltaic cell 560. The transmission unit 580 can be configured to transmit a signal in response to a voltage generated by the fluid-activated voltaic cell 560. The transmission unit 580 can be configured to transmit a signal in response to a voltage and a current generated by the fluid-activated voltaic cell 560. Electrical power, including current and voltage, generated by the redox reaction in the fluid-activated voltaic cell 560 powers signal transmission from the transmission unit 580. One or more connectors 595, such as wire, electrically connects the transmission unit 580 and the fluid-activated voltaic cell 560.

In some embodiments, a converter can be operably connected between the transmission unit 580 and the fluid-activated voltaic cell 560, connected with the one or more connectors 595. In some embodiments, a current to voltage boost converter can be included along the connector 595 between the transmission unit 580 and the fluid-activated voltaic cell 560. In some embodiments, a current to voltage step-up converter can be included along the connector 595 between the transmission unit 580 and the fluid-activated voltaic cell 560. A converter can be operably attached to the fluid-activated voltaic cell 560 and to the transmission unit 580 with one or more connectors 595.

As illustrated in FIG. 5, an antenna 520 can be a substantially planar antenna, such as commonly used in radio frequency identification (RFID) or near field communication (NFC) units. The transmission unit 580 can include a RFID unit. The transmission unit 580 can include a NFC unit. The transmission unit 580 can include a unique identifier, such as a RFID identifier, to specify a specific transmission unit 580. Prior to use, the antenna 520 can be detuned with a removable surface layer of a conductive material. This can be desirable to reduce excess RFID signals, for example from appurtenances 120 in storage prior to attachment to a wound dressing. See U.S. Pat. No. 7,724,136 to Posamentier, titled "Revealable RFID Devices," which is incorporated herein by reference. The circuitry 530 of the transmission unit 580 can include a variety of components, as desired in a particular embodiment. The circuitry 530 of the transmission unit 580 can include a processor 535. The circuitry 530 can include non-volatile memory 550. The circuitry 530 can include a transmitter 540. The circuitry 530 can include one or more additional modules 545. For example, the circuitry 530 can include a receiver. For example, the circuitry 530 can include a transceiver. For example, the circuitry 530 can include an additional antenna. For example, the circuitry 530 can include volatile memory. For example, the circuitry 530 can include non-volatile memory. The circuitry 530 can include dielectric material configured to electrically interact with one or more antennas. See, for example, U.S. Pat. No. 7,055,754 to Forester, titled "Self-Compensating Antennas for Substrates Having Differing Dielectric Constant Values," which is incorporated herein by reference.

A transmission unit 580 can be configured to transmit a signal in response to an interrogation signal. A transmission unit 580 can include an energy harvesting unit, such as a unit configured to obtain energy from electromagnetic waves. A transmission unit 580 can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. A transmission unit 580 can include an oscillator and encoder configured to generate a programmable pulse position-modulated signal in the radio frequency range. See, for example, U.S. Pat. No. 4,384,288 to Walton, titled "Portable Radio Frequency Emitting Identifier," which is incorporated herein by reference. A transmission unit 580 can include a radio frequency identification device (RFID). A transmission unit 580 can be configured to be a transmitter of signals in the UHF range. A transmission unit 580 including an RFID device can be configured to transmit signals in the UHF standard range utilized in a global region, as illustrated in the "Worldwide RFID UHF Map" by Intelleflex Corporation (©2009), which is incorporated herein by reference. A transmission unit 580 can include a radio frequency identification device (RFID). See, for example, Chawla and Ha, "An Overview of Passive RFID," *IEEE Applications and Practice*, 11-17 (September 2007), which is incorporated herein by reference. A transmission unit 580 can include a battery-assisted passive RFID device, such as sold by Alien Technology®, Morgan Hill, Calif., such as described in the brochure from Alien Technology® titled "Battery Assisted Passive Tags" and incorporated herein by reference. A transmission unit 580 can include an optical transmitter unit. A transmitter unit can be configured to transmit at approximately 13.56 megahertz (MHz), or within the ISO 14443 standard parameters. See Patauner et al., "High Speed RFID/NFC at the Frequency of 13.56 MHz," presented at the *First International EURASIP Workshop on RFID Technology*, pages 1-4, 24-25 Sep. 2007, Vienna Austria, which is incorporated herein by reference. A transmission unit 580 can include at least two antennas. A transmission unit 580 can include a self-compensating antenna system. An antenna can include dielectric material configured to electrically interact with one or more antennas. See, for example, U.S. Pat. No. 7,055,754 to Forester, titled "Self-Compensating Antennas for Substrates Having Differing Dielectric Constant Values," which is incorporated herein by reference. A transmission unit 580 can include a hybrid backscatter system configured to function in an RFID, IEEE 802.11x standard and Bluetooth system. See, for example, U.S. Pat. No. 7,215,976 to Brideglall, titled "RFID Device, System and Method of Operation Including a Hybrid backscatter-based RFID Protocol Compatible with RFID, Bluetooth and/or IEEE 802.11x Infrastructure," which is incorporated herein by reference. A transmission unit 580 can be configured to transmit at approximately 131 kilohertz (KHz), for example as part of a RuBee™ (IEEE standard 1902.1) system (sold, for example, by Visible Assets™, Inc.). See for example: the description of RuBee™ systems from the Visible Assets™ webpage; Stevens et al., "RuBee (IEEE 1902.1)—The Physics Behind, Real-Time, High Security Wireless Asset Visibility Networks in Harsh Environments," a white paper from Visible Assets™; and in US Patent Application No. 2007/0171076 to Stevens and Waterhouse, titled "Low-frequency Radio Tag Encapsulating System," each of which are incorporated herein by reference. A transmission unit 580 can include a near field communication (NFC) device. A transmission unit 580 can include a Wireless Identification and Sensing Platform (WISP) device, manufactured by Intel Corporation, such as described in the "WISP: Wireless Identification and Sensing Platform" webpage (downloaded on Oct. 28, 2011) incorporated herein by reference. A transmission unit 580 can be operably coupled to a sensor, such as a sensor that detects changes in capacitance (see, e.g. Sample et al., "A Capacitive Touch Interface for Passive RFID Tags," 2009 *IEEE International Conference on RFID*, 103-109 (2009), which is incorporated herein by reference).

In some embodiments, the transmission unit 580 can include a pressure sensitive activation region, wherein the pressure sensitive activation region is configured to be activated by physical pressure between a surface of the substrate 585 and a surface of the wound dressing (e.g. surface 410 as illustrated in FIG. 4). In some embodiments, the transmission unit 580 can include a pressure sensitive activation region, wherein the pressure sensitive activation region is configured to be activated by physical pressure on a surface of the appurtenance 120. See, for example, U.S. Pat. Nos. 6,693,513 and 6,037,879 to Tuttle, titled "Wireless Identification Device, RFID Device with Push-On/Push-Off Switch, and Method of Manufacturing Wireless Identification Device," and U.S. Pat. No. 6,863,220 to Selker, titled "Manually Operated Switch for Enabling and Disabling an RFID Card," as well as Sample et al., "A Capacitive Touch Interface for Passive RFID Tags," 2009 *IEEE International Conference on RFID*, 103-109 (2009), which are each incorporated herein by reference. A transmission unit 580 can be operably coupled to a data storage unit, for example as described in U.S. Pat. No. 7,825,776 to Smith and Haehnel, titled "Device Configuration with RFID," and US Patent Application No. 2009/0243813 to Smith et al., titled "Wireless Programming of Non-Volatile Memory with Near-Field UHF Coupling," which are each incorporated herein by reference.

In some embodiments, the transmission unit 580 can include an acoustic transmitter. For example, a transmission unit 580 can include a piezoelectric speaker. A variety of suitable piezoelectric speakers are available, including from Murata Manufacturing Co., Ltd., with North American corporate headquarters in Smyrna, Ga. (see, e.g. the Murata catalog titled "Piezoelectric Sounds Components" labeled P37E and dated Jan. 28, 2010, which is incorporated herein by reference). Some embodiments can include acoustic transmitter units such as those manufactured by Advanced Telemetry Systems (headquartered in Isanti, Minn.) for the Pacific Northwest National Laboratory (see, e.g. JSATS Acoustic Transmitter information sheet from the Pacific Northwest National Laboratory, updated March 2010, which is incorporated herein by reference). In some embodiments, an appurtenance can include a piezoelectric speaker configured as part of an acoustic transmitter and also to act as a signaling device (e.g. to generate a beeping noise in response to a signal from the processor).

In some embodiments, the transmission unit 580 can include an ultrasonic transmitter. In some embodiments, the transmission unit 580 can include an ultrasonic transducer. Multiple examples of ultrasonic transmitters and transducers are commercially available, often marketed under the term "ultrasonic sensors" as it is used in the industry (see, e.g. the Murata catalog titled "Ultrasonic Sensor" labeled 515E and dated Oct. 31, 2008, which is incorporated herein by reference). The transmitter unit can be configured as part of an ultrasonic ranging system. See: Wang, "A Design Method of Ultrasonic Ranging System with High Accuracy," *Journal of Computational Information Systems*, 7: 7 pages 2444-2451 (2011), which is incorporated herein by reference. The transmission unit 580 can be configured to communicate with an ultrasonic communication system. See: Chen and Wu, "Ultrasonic System with Infrared Communication Technology," *Journal of Computers*, vol. 6, no. 11, pages 2468-2475 (2011), which is incorporated herein by reference.

In some embodiments, the transmission unit 580 can include an optical transmitter. For example, an optical transmitter unit can include one or more light emitting diodes (LEDs). For example, an optical transmitter unit can include an infrared laser. In some embodiments, optical transmitter units can be desirable to minimize interference from nearby electrical equipment, such as medical equipment. See: Kavehrad, "Sustainable Energy-Efficient Wireless Applications Using Light," *IEEE Communications Magazine*, vol. 48, no. 12, pages 66-73, (2010); and Fadlullah and Kavehrad, "Indoor High-Bandwidth Optical Wireless Links for Sensor Networks" *Journal of Lightwave Technology*, vol. 28, no. 21, pages 3086-3094 (2010), which are incorporated herein by reference.

Some embodiments can include one or more additional transmission units distinct from the transmission unit 580 attached to the fluid-activated voltaic cell 560. An additional transmission unit can be configured to utilize received signals as an energy source. For example, an additional transmission unit can include a passive RFID unit. An additional transmission unit can include an attached power source, such as a battery. For example, an additional transmission unit can include, for example, an active RFID unit and an attached thin-film battery. An additional transmission unit including an RFID unit can be included, for example, as part of an inventory control device included with the appurtenance. An additional transmission unit including an RFID unit can be included, for example, as part of a patient identification system, such as implemented in a hospital or care facility. An additional transmission unit can be, for example, an optical energy emitter, such as an LED or other light emitting device. An additional transmission unit can be, for example, an auditory emitter, such as a piezoelectric speaker or other sound emitter. An additional transmission unit can be, for example, a vibration emitter, such as a piezoelectric device.

FIG. 5 illustrates that the appurtenance 120 affixed to a wound dressing to form a wound dressing-appurtenance combination unit 125 includes a projection 200. Although the projection 200 is displayed for the purposes of illustration, when an appurtenance 120 is affixed to a wound dressing to form a wound dressing-appurtenance combination unit 125 in normal use, the projection 200 would extend into an interior region of the wound dressing (see, e.g. FIG. 2B), and, therefore, not be visible from a superficial view. The projection 200 is configured to allow fluid flow from an interior region of the wound dressing into an interior region of the appurtenance 120. As illustrated in FIG. 5, in some embodiments the projection 200 can include a substantially hollow tubular structure. The projection 200 can be a substantially hollow tubular structure with an opening 590 at the end distal to the appurtenance. The projection 200 can be of a size and shape to project underneath one or more superficial structures of the wound dressing when the wound dressing is in use. The projection 200 can be of a size and shape to project through a width of the wound dressing when the appurtenance is attached to the wound dressing. In some embodiments, the projection 200 is fabricated from a plastic material. For example, the projection 200 can be fabricated from a pliable plastic material. For example, the projection 200 can be fabricated from a bio-compatible plastic material. For example, the projection 200 can be fabricated from a plastic material that can be sterilized prior to use of the appurtenance 120. The projection 200 illustrated in FIG. 5 includes an opening 590 at the end of the projection 200 distal to the end of the projection 200 adjacent to the substrate 585. The projection 200 can be of a size and shape to project from the outer surface of the wound dressing to within layers of the wound dressing. FIG. 5 depicts a fluid-activated voltaic cell 560 attached to the projection 200. The fluid-activated voltaic cell 560 includes an internal region 575. The projection 200 is configured to allow fluid flow from the interior of the wound dressing 500 through the opening 590 of the projection 200 into the internal region 575 of the fluid-activated voltaic cell 560. The projection 200 illustrated in FIG. 5 includes a substantially hollow tube with a first aperture 590 at a location adjacent to the interior region of the wound dressing and a second aperture at a location adjacent to the surface of the fluid-activated voltaic cell 560. In some embodiments, there are a plurality of projections 200.

The wound dressing-appurtenance combination unit 125 is configured so that fluid from an interior region of a wound dressing can flow into the projection 200 through the opening 590. Such fluid flow can occur, for example, when the wound dressing includes excessive levels of wound fluid (e.g. blood, pus) that moves into the projection 200 through the opening 590 from capillary action or in response to a pressure difference between the interior of the wound dressing and the interior of the projection and the internal region 575 of the fluid-activated voltaic cell 560. The fluid-activated voltaic cell 560 can include a chamber attached to a conduit, wherein the chamber is configured to receive the fluid from the external region. The fluid within the interior region 575 of the fluid-activated voltaic cell 560 serves as an electrolyte and activates the redox reaction of the electrodes 555, 565. The resulting current powers the transmission unit 580 and initiates the sending of a signal from the transmission unit 580. No electrical power from the redox reaction of the electrodes 555, 565 need be stored by the system, such as in the circuitry 530. The current from the redox reaction of the electrodes 555, 565 directly powers the transmission unit 580 at the same time as the redox reaction is occurring. It is expected that the current from the redox reaction of the electrodes 555, 565 will last for a brief time, on the order of minutes, and the signal transmitted from the transmission unit 580 will similarly occur for a brief time. Therefore, the wound dressing-appurtenance combination unit 125 will generate a real-time signal that a wound dressing has excessive internal fluid, and therefore that it should be checked by a caregiver. In some embodiments, the signal from the wound dressing-appurtenance combination unit 125 is received by an external device that contains memory, and therefore can maintain a persistent indicator that the wound dressing requires attention. See, e.g. FIGS. 12 and 13 and associated text.

Some embodiments include a sensor. A sensor can be operably attached, for example, to a projection 200. A sensor can be operably attached, for example, to a transmission unit 580. A transmitter unit 580 can be operably coupled to a sensor, such as a sensor that detects changes in capacitance (see, e.g. Sample et al., "A Capacitive Touch Interface for Passive RFID Tags," 2009 *IEEE International Conference on RFID*, 103-109 (2009), which is incorporated herein by reference). A transmitter unit 580 can be operably coupled to a sensor, such as described in: Ruhanen et al., "Sensor-enabled RFID Tag and Handbook," from *Building Radio Frequency Identification for the Global Environment* (2008); Sample et al., "Design of an RFID-Based Battery-Free Programmable Sensing Platform," *IEEE Transactions on Instrumentation and Measurement*, vol. 57, no. 11, 2608-2615 (2008); Yeager et al., "Wirelessly-Charged UHF Tags for Sensor Data Collection," 2008 IEEE International Conference on RFID, Apr. 16-17, 2008, pages 320-327; U.S. Pat. Nos. 5,904,671 and 6,348,640 to Navot and Botton, each titled "Tampon Wetness Detection System;" U.S. Pat. No. 7,446,660 to Posamentier titled "Passive Environmental RFID Transceiver;" and U.S. Pat. No. 5,704,352 to Tremblay and Buckles, titled "Implantable Passive Bio-Sensor," which are each incorporated herein by reference. A sensor can be operably attached, for example, to a substrate 585. A sensor can be operably attached, for example, to a fluid-activated voltaic cell 560. "Sensors," as used herein, can be of a variety of types depending on the embodiment. One or more sensors can include at least one sensor responsive to changes in capacitance, or a measure of the ability of a configuration of materials to store electric charge. A general review of biosensors that detect changes in the dielectric properties of an electrode surface can be found in Berggren et al., "Capacitive Biosensors," *Electroanalysis* vol. 13, no. 3, 173-180, (2001), which is incorporated herein by reference. For example, one or more sensors can include a micromechanical biosensor with a fixed-fixed beam attached to an interdigitated capacitor (see, for example, Lim et al., "A Micromechanical Biosensor with Interdigitated Capacitor Readout," *Proceedings of the 2011 IEEE/ICME International Conference on Complex Medical Engineering*, May 22-25, Harbin, China, which is incorporated herein by reference). Sensors can also include nanowire nanosensors, for example as described in Cui et al., "Nanowire Nanosensors for Highly Sensitive and Selective Detection of Biological and Chemical Species," *Science*, vol. 293, 1289-1292 (2001), which is incorporated herein by reference. Sensors can include those utilizing antibodies secured to a graphene substrate. See Tehrani et al., "Detection of Monoclonal Antibodies using Chemically Modified Graphite Substances," *IEEE Sensors 2010 Conference Proceedings*, 428-431, (2010), which is incorporated herein by reference. In some embodiments, sensors include aptamer-modified graphene field-effect transistors, see Ohno et al., "Graphene Field-Effect Transistors for Label-Free Biological Sensors," *IEEE Sensors 2010 Conference Proceedings*, 903-906, (2010), which is incorporated herein by reference. A sensor in an appurtenance can interact with a sensor present in a wound dressing, for example as described in U.S. Pat. No. 6,283,938 to McConnell, titled "Medicating Bandage and Controllable Permeable Membrane," which is incorporated herein by reference. A sensor can include a field effect transistor (FET), such as described in U.S. Pat. No. 7,507,675 to Zuilhof et al., titled "Device Manufacturing Method and Device," which is incorporated herein by reference. A sensor can include a nano-cantilever device, such as described in U.S. Pat. No. 7,612,424 to Espinosa and Ke, titled "Nanoelectromechanical Bistable Cantilever Device," which is incorporated herein by reference. A sensor can be configured to provide information regarding the wound dressing and associated fluid, such as temperature, presence of specific analytes in the fluid, or relative wetness of the dressing as a whole. A variety of sensors can be utilized in different embodiments of the appurtenances, depending on factors such as the intended use of the appurtenance, size, weight, cost, bio-compatibility, safety and ease of disposal.

Figure 6:
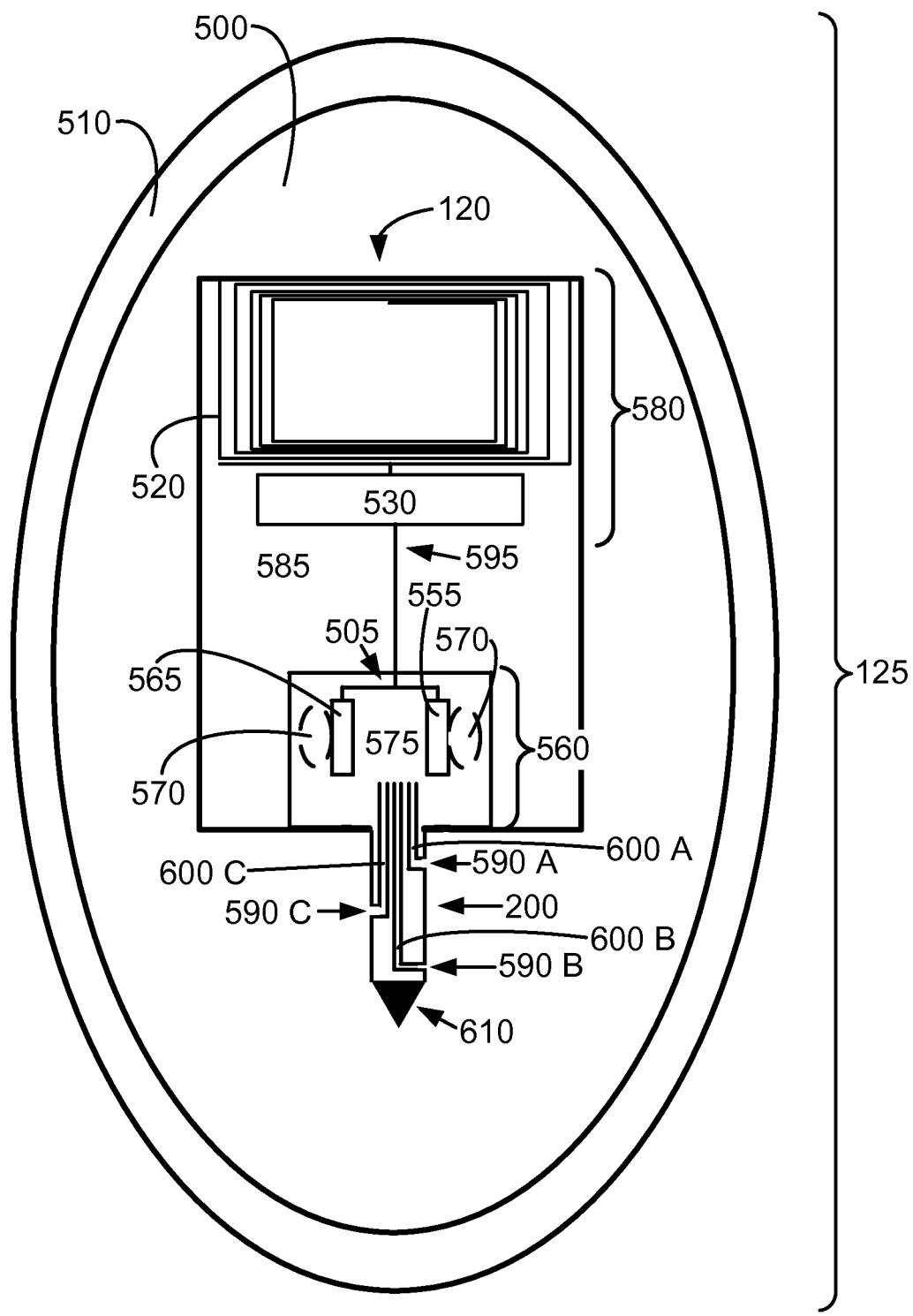
FIG. 6 is a schematic of an appurtenance to a wound dressing.

FIG. 6 depicts a wound dressing-appurtenance combination unit 125. The wound dressing-appurtenance combination unit 125 of FIG. 6 is shown in a "top-down," external view, similar to that of FIG. 5. As illustrated in FIG. 6, the wound dressing-appurtenance combination unit 125 includes a wound dressing with a wound covering region 500 and an edge region 510. The appurtenance 120 includes a substrate 585. The appurtenance 120 includes a transmission unit 580. The transmission unit 580 includes an antenna 520 and circuitry 530. A connector 595 is configured to provide an electrical connection between the transmission unit 580 and a fluid-activated voltaic cell 560. The connector 595 is configured to provide electrical current to the transmission unit 580 from the fluid-activated voltaic cell 560. The fluid-activated voltaic cell 560 includes a first electrode 555 and a second electrode 565 joined with an electrical connector 505, such as a wire. The electrical connector 505 is joined to the connector 595 to provide an electrical connection between the transmission unit 580 and the fluid-activated voltaic cell 560. The fluid-activated voltaic cell 560 includes an internal region 575 between the first electrode 555 and a second electrode 565, the internal region 575 configured to accept fluid flow through the projection 200. The fluid-activated voltaic cell 560 includes two enhancement units 570 positioned adjacent to each of the first electrode 555 and a second electrode 565.

The projection 200 shown in FIG. 6 includes a plurality of apertures 590 A, B, C located along the length of the projection 200. Each of the apertures 590 A, B, C will be positioned adjacent to a distinct region of the interior of the wound dressing when the projection 200 is inserted within the wound dressing (not shown in FIG. 6 for purposes of illustration). Each of the apertures 590 A, B, C is connected to a conduit 600 A, B, C within the projection 200. Each conduit 600 A, B, C includes a first end attached to an aperture 590 A, B, C and a second end attached to the fluid activated voltaic cell 560. Each of the conduits 600 A, B, C is configured to direct fluid from the interior region of the wound dressing into the interior region 575 of the fluid-activated voltaic cell 560. As shown in FIG. 6, each of the conduits 600 A, B, C projects into the interior region 575 of the fluid-activated voltaic cell 560. In some embodiments, the projection 200 is partially positioned within the fluid-activated voltaic cell 560 and the projection 200 includes an aperture within the fluid-activated voltaic cell 560. Also as illustrated in FIG. 6, in some embodiments the projection 200 includes a region 610 configured to facilitate insertion of the projection 200 into the wound dressing 500. For example, the projection 200 can include a region 610 configured as a tapered point on the distal end of the projection 200.

Some embodiments include a passive RFID unit including an identifier. In some embodiments, the passive RFID unit can be integrated into the transmission unit 580. In some embodiments, the passive RFID unit can be a distinct unit of the appurtenance 120. The passive RFID can be configured, for example, as an positioning control unit to confirm the presence of the appurtenance 120 in a specific location, such as in association with a specific patient or wound dressing.

Figure 7:
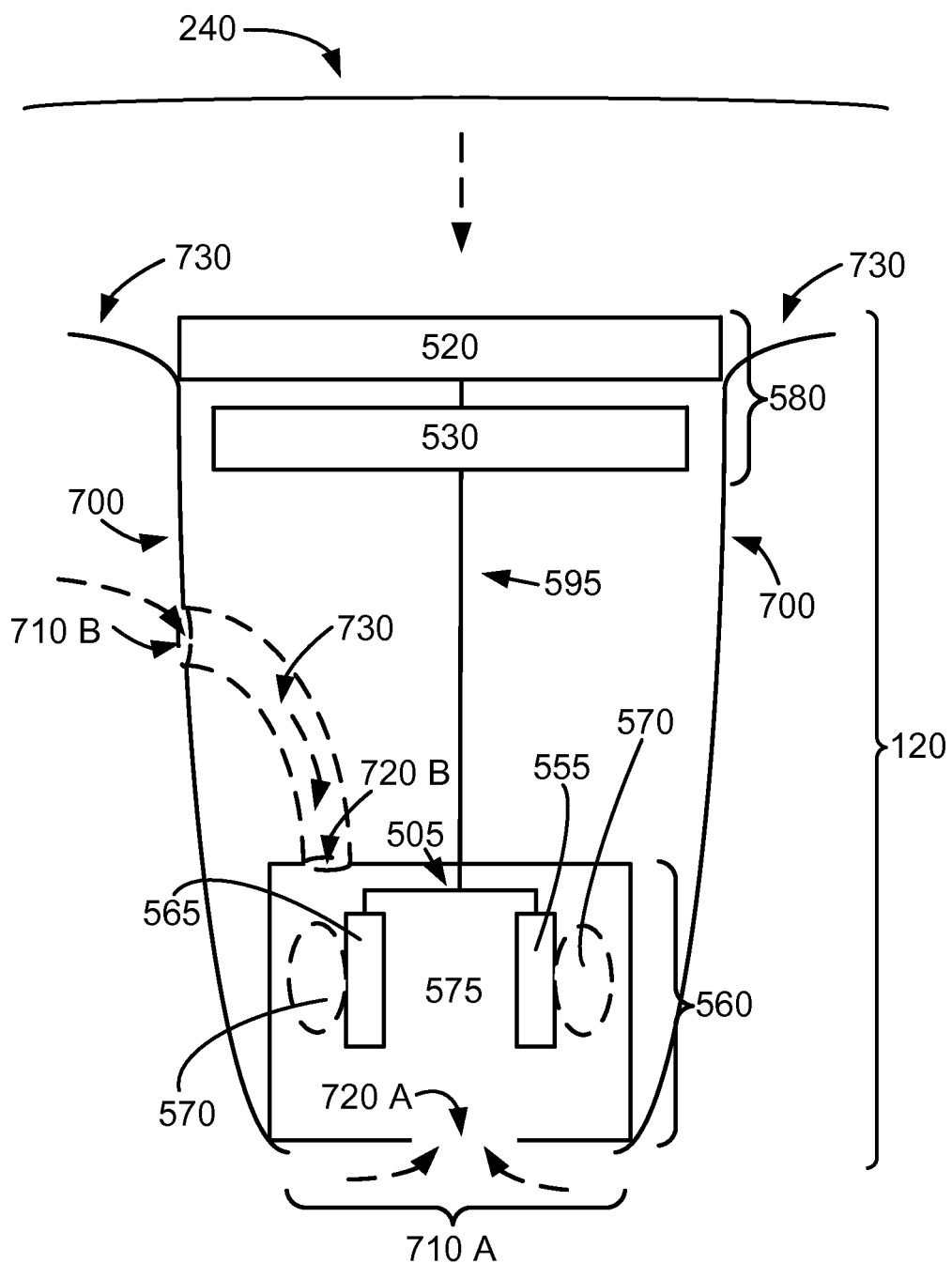
FIG. 7 is a schematic of an appurtenance to a wound dressing.

FIG. 7 illustrates aspects of an embodiment of an appurtenance 120, such as that depicted in FIGS. 3A and 3B. The appurtenance 120 depicted in a cross-sectional view in FIG. 7 includes an enclosure 700 of a height and width to fit substantially within an interior region of a wound dressing (see, e.g. FIG. 3B). The appurtenance 120 depicted in a cross-sectional view in FIG. 7 includes an enclosure 700 of a height and width to fit substantially within an interior region of a wound dressing, the enclosure 700 including at least one aperture 710 A, B configured to allow fluid to flow from the interior region of the wound dressing into the enclosure 700 (see dotted arrows). The appurtenance 120 depicted in FIG. 7 also includes a fluid-activated voltaic cell 560 attached to one or more of the at least one aperture 710 A, B. The appurtenance 120 shown in FIG. 7 includes a transmission unit 580 attached to an internal surface of the enclosure 700, the transmission unit 580 including circuitry 530 and at least one antenna 530, the transmission unit 580 configured to transmit a signal in response to the fluid-activated voltaic cell 560. A wire connector 595 connects the transmission unit 580 to the fluid-activated voltaic cell 560, the wire connector 595 configured to conduct current from the fluid-activated voltaic cell 560 to the transmission unit 580. Some embodiments can include a passive RFID unit, including an identifier. The appurtenance 120 illustrated in FIG. 7 includes an enclosure 700 with substantially vertical walls tapering to an aperture 710 A at a position corresponding to an interior region of a wound dressing when the appurtenance 120 is in use. A fluid-activated voltaic cell 560 is positioned within the enclosure 700 adjacent to the aperture 710 A. The fluid-activated voltaic cell 560 includes an opening 720 A adjacent to the aperture 710 A of the enclosure 700. As shown in FIG. 7, in some embodiments an enclosure 700 includes a plurality of apertures 710 A, 710 B. FIG. 7 illustrates a second aperture 710 B in the wall of the enclosure 700, the second aperture 710 B connected to a conduit 730. The conduit 730 is connected to an opening 720 B in the fluid-activated voltaic cell 560 at an end of the conduit 730 distal to the second aperture 710 B.

Some embodiments include a microcapillary film within at least one aperture 710 A, 710 B, the microcapillary film configured to direct fluid from an interior region of the wound dressing into the interior of the enclosure 700. See, for example, U.S. Pat. No. 6,420,622 to Johnston, "Medical Article Having Fluid Control Film," which is incorporated by reference herein. Some embodiments include a porous film or mesh within at least one aperture 710 A, 710 B, configured to allow fluid flow from an interior region of the wound dressing into the interior of the enclosure 700 and to minimize other matter entering the appurtenance (e.g. structural portion of the wound dressing or wound debris).

The enclosure 700 depicted in FIG. 7 is a vertical, cross sectional view of a substantially cone shaped enclosure 700. As shown in FIGS. 3A, 3B and 7, in some embodiments the enclosure 700 is a substantially cylindrical structure, wherein the largest width of the substantially cylindrical structure is less than the smallest width of the wound dressing. In some embodiments, the enclosure 700 is a substantially pyramidal structure, wherein the largest width of the substantially pyramidal structure is less than the smallest width of the wound dressing. In some embodiments, the enclosure 700 includes a substantially conical or a substantially conical frustum shaped structure. In some embodiments, the enclosure 700 includes a cross-sectional view square area (i.e. substantially at right angles to the view illustrated in FIG. 7) that is substantially equal to or less than one tenth of a square area of a largest surface of the wound dressing. As shown in FIG. 7, the enclosure 700 includes one or more flanges 730 at the upper edge of the substantially conical structure of the enclosure 700. The flanges 730 are positioned to locate the enclosure 700 relative to an outer surface of a wound dressing, and can be positioned to provide a surface for attachment of a cover 240 (see, e.g. FIG. 3B). A flange 730 can include a flange region configured to cover part of an outer surface of the wound dressing when the appurtenance 120 is positioned for use with the wound dressing. One or more flanges 730 can be located on the enclosure 700 in a manner to functionally inhibit the movement of the enclosure 700 into the interior of the wound dressing layer. The one or more flanges 730 can be located on the enclosure 700 in a manner to expand a portion of the circumference of the enclosure 700 and prevent the appurtenance 120 from moving into the wound dressing beyond that expanded circumference. The enclosure 700 can include one or more barbs positioned to hold the appurtenance 120 in place relative to the affixed wound dressing and to prevent the appurtenance 120 from slipping relative to the wound dressing. In some embodiments, the enclosure 700 includes one or more walls, the walls forming a flange 730 on an edge of the enclosure 700, the flange 730 positioned to attach a fastener between a surface of the wound dressing and the enclosure 700. In some embodiments, the enclosure 700 includes one or more walls, the walls forming a flange 730 on an edge of the enclosure 700, the flange 730 including one or more projections from a surface of the flange 730, the one or more projections positioned to pierce an outer surface of a wound dressing. For example, one or more flanges 730 can include one or more barbs, points or projections positioned to pierce an outer surface of a wound dressing and assist in maintaining the position of the appurtenance relative to the wound dressing. In some embodiments, an enclosure 700 can be formed as a substantially hollow tube.

Depending on the embodiment, the enclosure 700 of the appurtenance 120 can be fabricated from a variety of materials. For example, the enclosure 700 of the appurtenance 120 can be fabricated from at least one plastic material. For example, the enclosure 700 of the appurtenance 120 can be fabricated from bio-compatible materials. In some embodiments, the enclosure 700 of the appurtenance 120 can be covered or coated to increase functionality. For example, the enclosure 700 of the appurtenance 120 can be covered with bio-compatible materials on an external surface of the enclosure 700. For example, the enclosure 700 of the appurtenance 120 can be covered with a textured material to reduce potential slippage of the enclosure 700 within a wound dressing (see FIG. 3B).

Some embodiments include a fastener configured to form a seal between an edge of an enclosure 700 and a surface of a wound dressing. For example, an edge of an enclosure 700 can include an adhesive configured to seal the edge of the enclosure 700 to a surface of the wound dressing. For example, as illustrated in FIG. 7, the fastener can include a substantially planar cover 240 with an upper surface and a lower surface, the lower surface conforming to both the edge of the enclosure 700 and to the surface of the wound dressing, and adhesive on at least a portion of the substantially planar cover 240. Some embodiments include a piercing region operably attached to an edge of the enclosure 700 distal to an edge of the enclosure 700 adjacent to an outer surface of the wound dressing when the appurtenance is positioned for use with the wound dressing. For example, the enclosure 700 can include a tip, point, edge or surface projection configured to pierce a wound dressing surface when the appurtenance is affixed to the wound dressing.

FIG. 7 also includes a fluid-activated voltaic cell 560 attached to both of the apertures 710 A, 710 B in the enclosure 700. The fluid-activated voltaic cell 560 includes two electrodes 555, 565, electrically connected with a wire connection 505. The first electrode 555 and the second electrode 565 are positioned with an interior region 575 of the fluid-activated voltaic cell 560 between them. In some embodiments, the fluid-activated voltaic cell 560 includes at least one anode and at least one cathode. In some embodiments, the fluid-activated voltaic cell 560 includes at least one enhancement unit 570, the enhancement unit 570 configured to release at least one chemical enhancer of an electrochemical reaction within the fluid-activated voltaic cell 560 in response to contact with a fluid. In some embodiments, the at least one enhancement unit 570 includes at least one dry acid unit configured to release acid when contacted by a liquid. The interior region 575 of the fluid-activated voltaic cell 560 is configured to receive fluid flow through the aperture 710 A, B (illustrated as dotted arrows in FIG. 7). In some embodiments, the fluid-activated voltaic cell 560 includes a chamber configured to receive the fluid. As illustrated in FIG. 7, the apertures 710 A, 710 B can be oriented adjacent to different regions of the wound dressing when the appurtenance 120 is in place, and therefore to sample any potential wound liquids present in the different regions of the wound dressing.

In some embodiments with enclosures such as illustrated in FIG. 7, there can be a second fluid-activated voltaic cell 560 attached to at least one second aperture 710 B, the at least one second aperture 710 B configured to allow fluid to flow from a second interior region of the wound dressing into an interior of the second fluid-activated voltaic cell 560. See also FIG. 8. Some embodiments can include a sensor attached to at least one aperture 710 A, 710 B of the enclosure 700, and a connection between the sensor and the transmission unit 580. For example, the sensor can be operably coupled to the electrochemical circuit formed by the fluid-activated voltaic cell 560 and the transmission unit 580, so that the sensor is activated by current from the fluid-activated voltaic cell 560. For example, there may be a wire connection between the sensor and the transmission unit 580.

Figure 8:
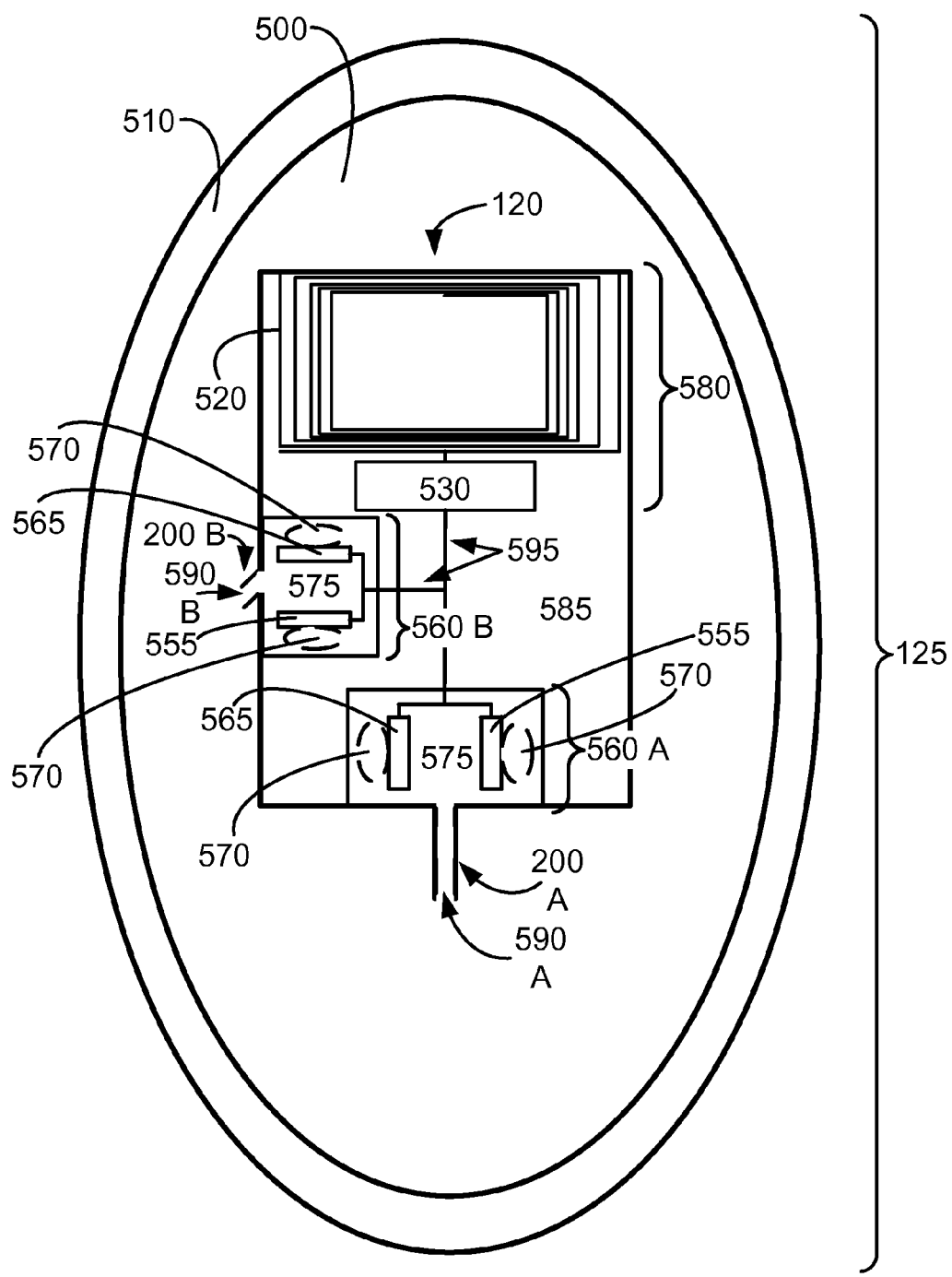
FIG. 8 is a schematic of an appurtenance to a wound dressing.

FIG. 8 illustrates an appurtenance 120 attached to a wound dressing 500, 510 and forming an appurtenance affixed to a wound dressing combination unit, 125. The view of FIG. 8 is similar to those of FIGS. 5 and 6. The appurtenance 120 shown in FIG. 8 includes a substrate 585. The appurtenance 120 includes two projections 200 A, 200 B. The projections 200 A, 200 B are positioned at different faces of the appurtenance 120. The projections 200 A, 200 B are of different lengths and project at different angles (e.g. the angle shown as θ in FIGS. 2 A and 2 B) from the plane of the substrate 585 of the appurtenance 120. Each of the individual projections 200 A, 200 B includes an opening 590 A, 590 B. Each of the openings 590 A, 590 B is positioned to be adjacent to a different region of the interior of the wound dressing 510. The individual projections 200 A, 200 B can, therefore, be considered to be sampling different regions of the interior of the wound dressing 510 when the appurtenance affixed to a wound dressing combination unit, 125 is in use.

Some embodiments include a microcapillary film within at least one opening 590 A, 590 B, the microcapillary film configured to direct fluid from an interior region of the wound dressing into the interior of the projection 200. See, for example, U.S. Pat. No. 6,420,622 to Johnston, "Medical Article Having Fluid Control Film," which is incorporated by reference herein. Some embodiments include a porous film or mesh within at least one opening 590 A, 590 B, configured to allow fluid flow from an interior region of the wound dressing into the interior of the projection 200 and to minimize other matter entering the appurtenance (e.g. structural portion of the wound dressing or wound debris).

Each of the projections 200 A, 200 B illustrated in FIG. 8 is operably attached to a fluid-activated voltaic cell 560 A, 560 B. Each of the fluid-activated voltaic cells 560 A, 560 B includes a first electrode 555 and a second electrode 565 connected with a wire connection 505. Each of the fluid-activated voltaic cells 560 A, 560 B includes an interior region 575 between the first electrode 555 and the second electrode 565. Each of the fluid-activated voltaic cells 560 A, 560 B includes an enhancement unit 570 adjacent to each of the electrodes 555, 565. A wire connector 595 couples the fluid-activated voltaic cells 560 A, 560 B to a single transmission unit 580. The transmission unit includes circuitry 530 and an antenna 520.

In the embodiment illustrated in FIG. 8, a fluid, such as blood or pus, present in the region of the wound dressing adjacent to either of the respective projection 200 A, 200 B openings 590 A, 590 B would flow into the projection 200 A, 200 B through the respective opening 590 A, 590 B. The presence of liquid in the interior region 575 between the first electrode 555 and the second electrode 565 acts as an electrolyte for the electrochemical reaction of the respective fluid-activated voltaic cell 560 A, 560 B. Current generated by the electrochemical reaction would move through the wire connector 595 and into the transmission unit 580, activating the transmission unit 580. Therefore, in the conformation illustrated in FIG. 8, excess liquid from the wound dressing in either the region of the wound dressing adjacent to either of the respective projection 200 A, 200 B openings 590 A, 590 B would initiate the electrochemical reaction of the respective fluid-activated voltaic cell 560 A, 560 B, resulting in a signal being generated by the transmission unit 580.

Figure 9:
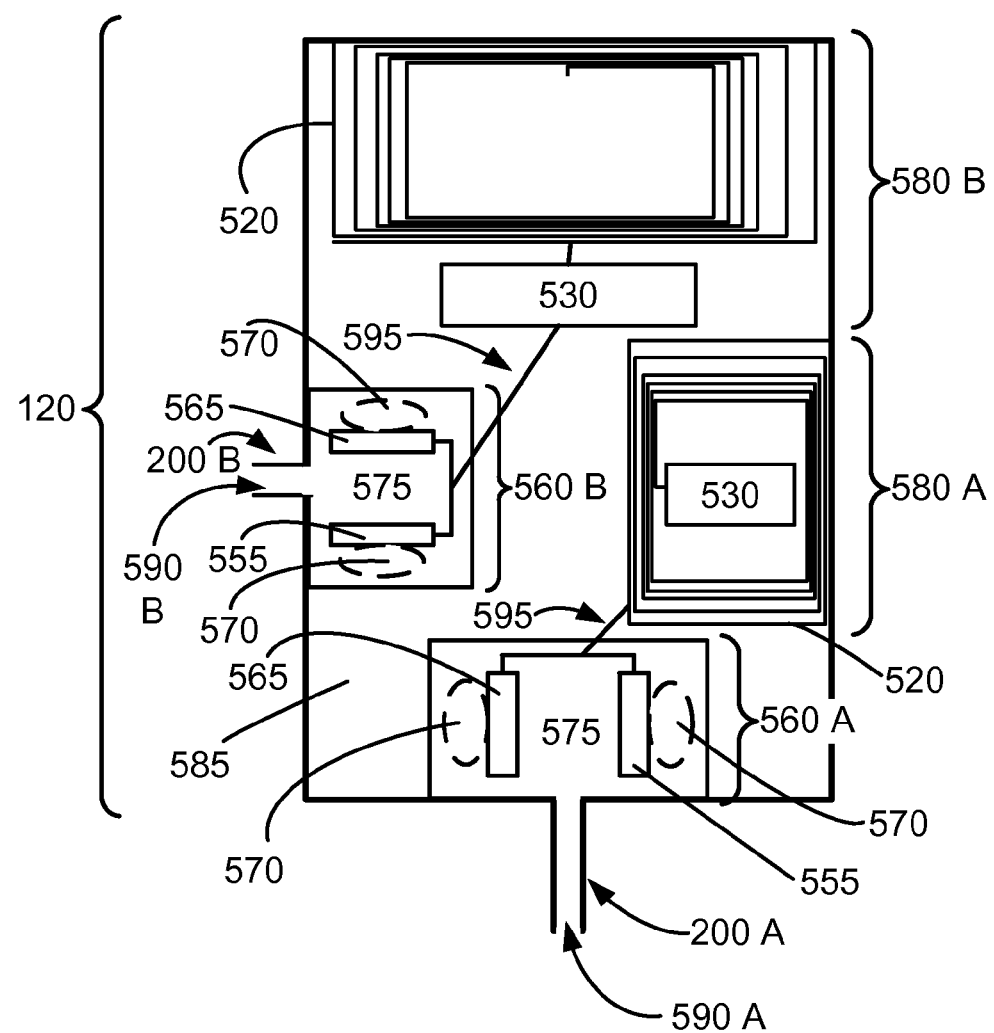
FIG. 9 is a schematic of an appurtenance to a wound dressing.

FIG. 9 illustrates an appurtenance 120 to a wound dressing. The appurtenance 120 includes a substrate 585 and two projections, 200 A, 200 B, projecting from different sides of the substrate 585. As in FIG. 8, the embodiment illustrated in FIG. 9 includes projections, 200 A, 200 B of different lengths and angles (e.g. the angle shown as θ in FIGS. 2 A and 2 B) from the plane of the substrate 585 of the appurtenance 120. Therefore, the embodiment shown in FIG. 9 would sample fluid potentially present in different regions of a wound dressing. The different regions of a wound dressing can be vertically or horizontally in different planes of the wound dressing, or both. Each of the projections 200 A, 200 B is connected to its respective fluid-activated voltaic cell 560 A, 560 B. Each of the fluid-activated voltaic cells 560 A, 560 B includes a first electrode 555 and a second electrode 565 connected with a wire connection 505. Each of the fluid-activated voltaic cells 560 A, 560 B includes an interior region 575 between the first electrode 555 and the second electrode 565. Each of the fluid-activated voltaic cells 560 A, 560 B includes an enhancement unit 570 adjacent to each of the electrodes 555, 565. A wire connector 595 couples each of the fluid-activated voltaic cells 560 A, 560 B to a distinct transmission unit 580 A, 580 B. Each of the respective transmission units 580 A, 580 B includes circuitry 530 and an antenna 520. Each of the respective transmission units 580 A, 580 B is configured to transmit a signal in response to a current generated by a redox reaction in the attached fluid-activated voltaic cell 560 A, 560 B.

In the embodiment illustrated in FIG. 9, a fluid, such as blood or pus, present in the region of the wound dressing adjacent to either of the respective projection 200 A, 200 B openings 590 A, 590 B would flow into the projection 200 A, 200 B through the respective opening 590 A, 590 B. The presence of liquid in the interior region 575 between the first electrode 555 and the second electrode 565 acts as an electrolyte for the electrochemical reaction of the respective fluid-activated voltaic cell 560 A, 560 B. Current generated by the electrochemical reaction would move through the wire connector 595 and into the associated transmission unit 580 A, 580 B, activating the specific transmission unit 580 A, 580 B. Therefore, in the conformation illustrated in FIG. 9, excess liquid from the wound dressing in either the region of the wound dressing adjacent to either of the respective projection 200 A, 200 B openings 590 A, 590 B would initiate the electrochemical reaction of the respective fluid-activated voltaic cell 560 A, 560 B, resulting in a signal being generated by the specific transmission unit 580 A, 580 B. In a system wherein a signal transmitted from a specific transmission unit 580 A, 580 B could be distinguished from other potential signals, the region of the wound dressing from which the fluid was obtained can also be associated with the specific signal. Such information can be useful, for example, to specify the relative depth or width of the wound dressing where the fluid was present. Such information can be useful, for example, to specify if the fluid is widespread in the wound dressing (i.e. present in multiple locations).

Figure 10:
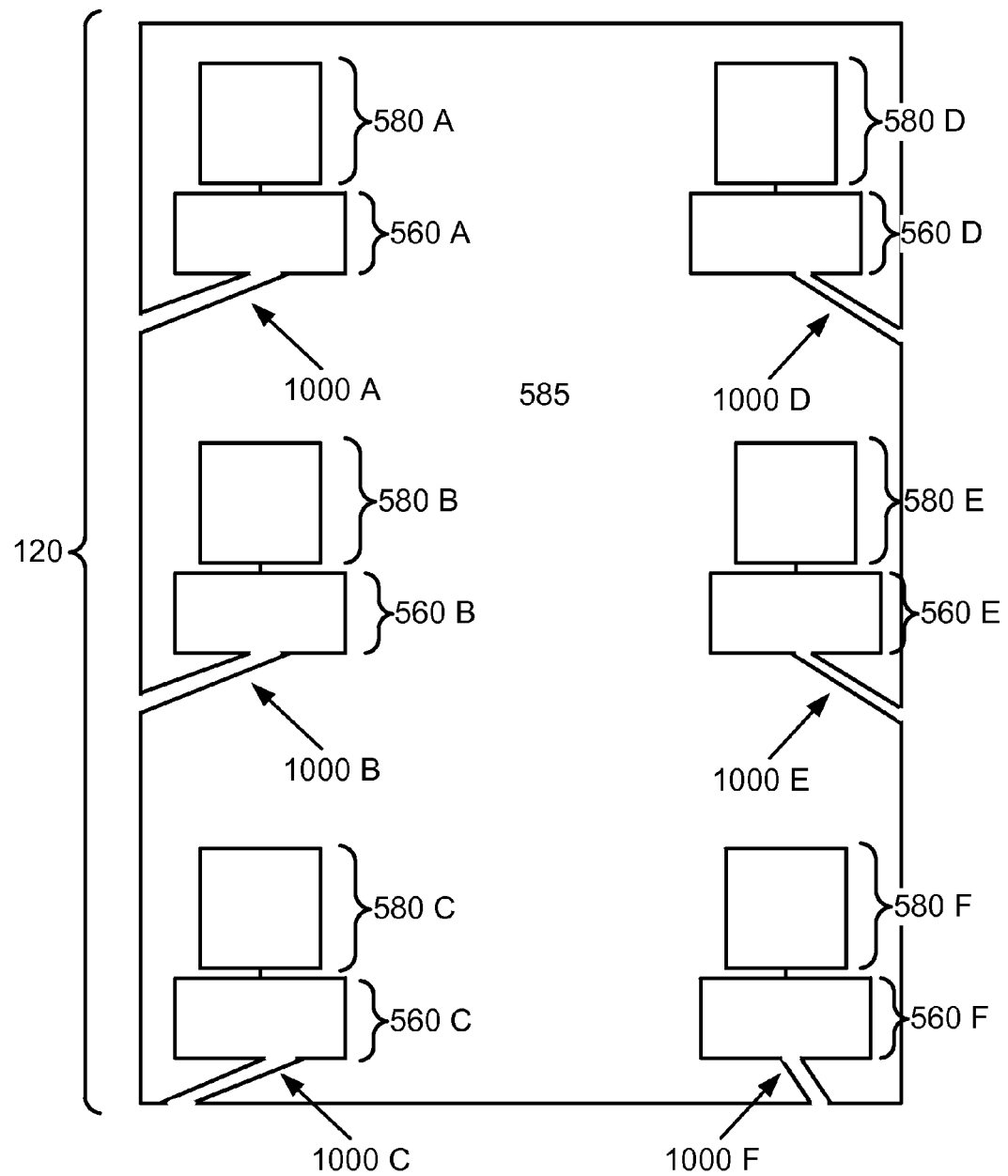
FIG. 10 is a schematic of an appurtenance to a wound dressing.

FIG. 10 depicts an appurtenance 120 to a wound dressing. The appurtenance 120 includes a substrate 585. As illustrated in FIG. 10, the appurtenance 120 includes a plurality of conduits 1000 A, B, C, D, E, F configured to direct fluid from a plurality of regions of a wound dressing adjacent to the appurtenance 120. Although the appurtenance 120 is illustrated in FIG. 10 as substantially planar, in some embodiments the appurtenance can include other three dimensional structures, such as cones, ellipses, cylinders, or a combination of shapes.

An appurtenance 120 can include one or more surfaces configured to mate with one or more surfaces of a wound dressing (not illustrated in FIG. 10). Each of the plurality of conduits 1000 A, B, C, D, E, F is positioned to allow fluid from an adjacent region of a wound dressing to flow through the conduit 1000 A, B, C, D, E, F into the attached fluid-activated voltaic cell 560 A, B, C, D, E, F. A conduit 1000 A, B, C, D, E, F can include features configured to encourage the flow of fluid from an adjacent region of a wound dressing to flow through the conduit 1000 A, B, C, D, E, F. For example, a conduit 1000 A, B, C, D, E, F can include a plurality of microchannels configured to direct fluid flow from the exterior of the appurtenance 120 into the fluid-activated voltaic cell 560 A, B, C, D, E, F. See, for example, U.S. Pat. No. 6,420,622 to Johnston, "Medical Article Having Fluid Control Film," which is incorporated by reference herein. For example, one or more of the conduits 1000 A, B, C, D, E, F can include a projection extending into the region surrounding the appurtenance, the projection configured to direct fluid flow from the exterior of the appurtenance 120 into the fluid-activated voltaic cell 560 A, B, C, D, E, F. No projections are illustrated in FIG. 10, however examples are, inter alia, in FIGS. 2A, 2B, 5, 6, 8, 9 and 12. Each of the fluid-activated voltaic cells 560 A, B, C, D, E, F has an attached transmission unit 580 A, B, C, D, E, F. Each of the transmission units 580 A, B, C, D, E, F is configured to transmit a signal in response to current generated by the attached fluid-activated voltaic cell 560 A, B, C, D, E, F. In some embodiments, each of the transmission units 580 A, B, C, D, E, F transmits a distinct signal, i.e. a signal including a unique identifier of that transmission unit 580 A, B, C, D, E, F. The respective location(s) in the wound dressing with fluid flowing into the conduits 1000 A, B, C, D, E, F can, therefore, be derived from the distinct signal from generated by each of the transmission units 580 A, B, C, D, E, F.

Figure 11:
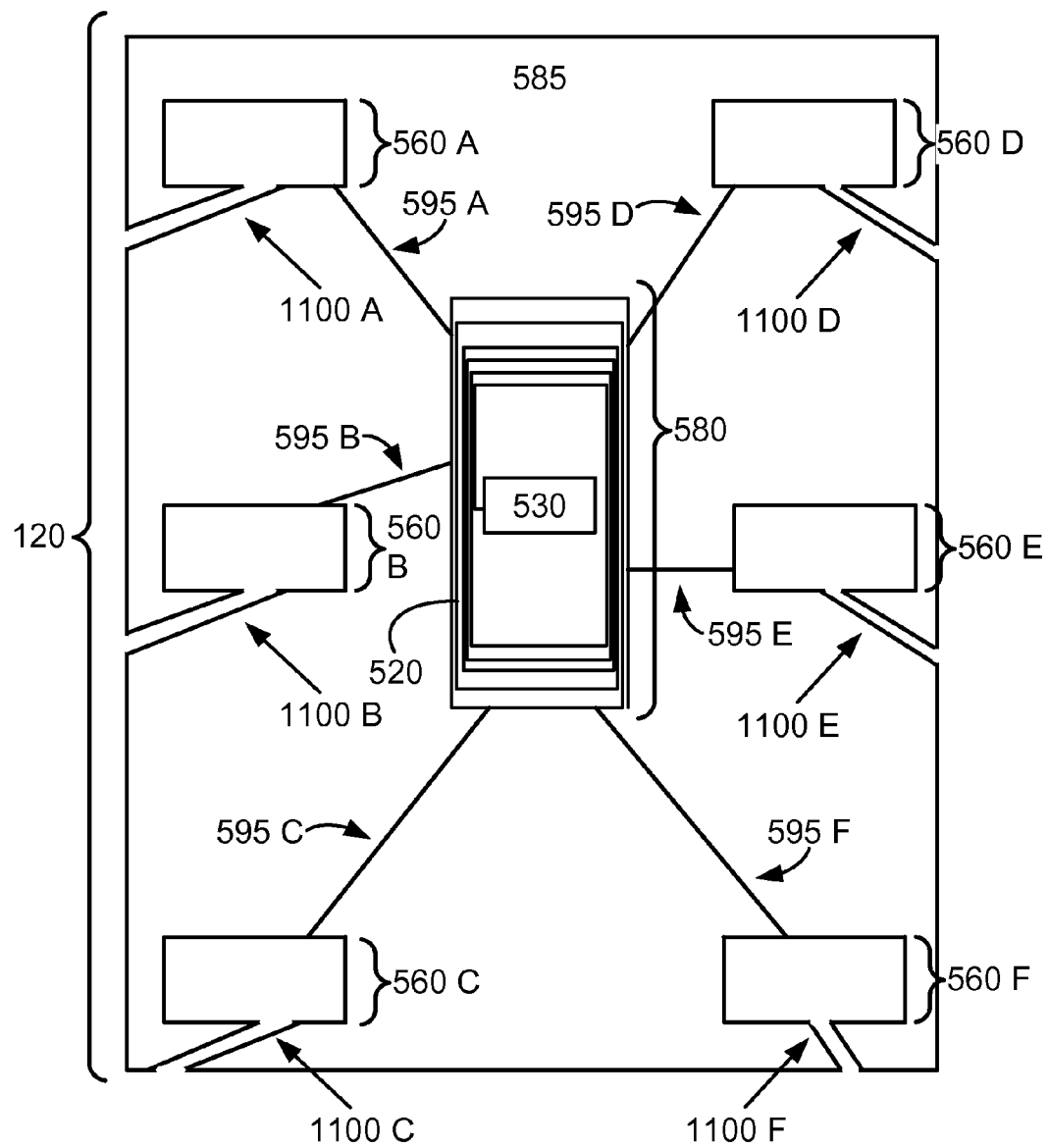
FIG. 11 is a schematic of an appurtenance to a wound dressing.

FIG. 11 depicts an appurtenance 120 to a wound dressing. The appurtenance 120 includes a substrate 585. As illustrated in FIG. 11, the appurtenance 120 includes a plurality of conduits 1100 A, B, C, D, E, F configured to direct fluid from a plurality of regions of a wound dressing adjacent to the appurtenance 120. Although the appurtenance 120 is illustrated in FIG. 11 as substantially planar, in some embodiments the appurtenance can include other three dimensional structures, which can include a combination of curvilinear structures. An appurtenance 120 can include one or more surfaces configured to mate with one or more surfaces of a wound dressing (not illustrated in FIG. 11). Each of the plurality of conduits 1100 A, B, C, D, E, F is positioned to allow fluid from an adjacent region of a wound dressing to flow through the conduit 1100 A, B, C, D, E, F into the attached fluid-activated voltaic cell 560 A, B, C, D, E, F. A conduit 1100 A, B, C, D, E, F can include features configured to encourage fluid from an adjacent region of a wound dressing to flow through the conduit 1100 A, B, C, D, E, F. For example, a conduit 1100 A, B, C, D, E, F can include a plurality of microchannels configured to direct fluid flow from the exterior of the appurtenance 120 into the fluid-activated voltaic cell 560 A, B, C, D, E, F. See, for example, U.S. Pat. No. 6,420,622 to Johnston, "Medical Article Having Fluid Control Film," which is incorporated by reference herein. For example, one or more of the conduits 1100 A, B, C, D, E, F can include a projection extending into the region surrounding the appurtenance, the projection configured to direct fluid flow from the exterior of the appurtenance 120 into the fluid-activated voltaic cell 560 A, B, C, D, E, F. No projections are illustrated in FIG. 11, however examples are, inter alia, shown in FIGS. 2A, 2B, 5, 6, 8, 9 and 12.

As illustrated in FIG. 11, each of the fluid-activated voltaic cells 560 A, B, C, D, E, F is attached to a transmission unit 580 with a wire connector 595 A, B, C, D, E, F. The transmission unit 580 includes an antenna 520 and circuitry 530. The transmission unit 580 is configured to send a signal in response to a current transmitted through one or more of the associated wire connectors 595 A, B, C, D, E, F from one or more of the fluid-activated voltaic cells 560 A, B, C, D, E, F. The transmission unit 580 of the appurtenance 120 illustrated in FIG. 11 is configured to send a series of signals in response to current generated by the fluid-activated voltaic cells 560 A, B, C, D, E, F in series. For example, the transmission unit 580 may be activated at a first time in response to a current generated by fluid-activated voltaic cell 560 A and carried by the wire connector 595 A from the fluid-activated voltaic cell 560 A to the transmission unit 580. For example, the transmission unit 580 may be activated at a second time in response to a current generated by fluid-activated voltaic cell 560 B and carried by the wire connector 595 B from the fluid-activated voltaic cell 560 B to the transmission unit 580. For example, the transmission unit 580 may be activated at a third time in response to a current generated by fluid-activated voltaic cell 560 C and carried by the wire connector 595 C from the fluid-activated voltaic cell 560 C to the transmission unit 580. The transmission unit 580 at further times can be activated by, for example, in response to current generated by fluid-activated voltaic cells 560 D, E and F.

Figure 12:
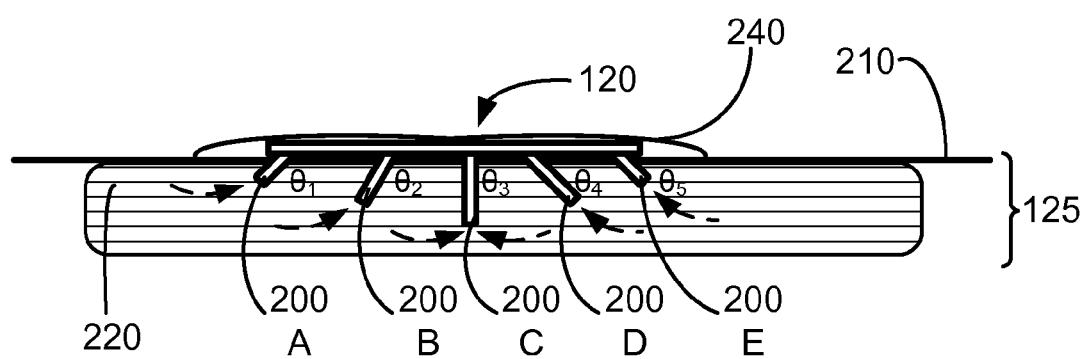
FIG. 12 is an illustration of an appurtenance to a wound dressing.

FIG. 12 illustrates an appurtenance 120 attached to a wound dressing 115 to form a wound dressing with an affixed appurtenance combination unit 125. The wound dressing with an affixed appurtenance combination unit 125 shown in FIG. 12 is illustrated in cross-section, similar to the views of FIGS. 2A and 2B. The wound dressing with an affixed appurtenance combination unit 125 includes a wound dressing portion including an outer layer 210 and a wound dressing layer 220. A cover 240 further adheres to the outer surface of the outer layer 210 and to an outer surface of the appurtenance 120.

The appurtenance 120 includes a plurality of projections 200 A, B, C, D and E. Each projection 200 A, B, C, D and E is configured to allow fluid flow from an adjacent region of the wound dressing interior, as illustrated by the dotted arrows. As shown in FIG. 12, the projections 200 A, B, C, D and E are spaced apart, so that they extend from different positions on the appurtenance 120. In addition, the projections 200 A, B, C, D and E are of different lengths. The projections 200 A, B, C, D and E also extend from the surface of the appurtenance at different angles, $\theta_1$, $\theta_2$, $\theta_3$, $\theta_4$, $\theta_5$. The combination of projections 200 A, B, C, D and E spaced apart on the appurtenance 120, of different lengths and extending at different angles, $\theta_1$, $\theta_2$, $\theta_3$, $\theta_4$, $\theta_5$ results in an appurtenance 120 that is configured to sample fluid from a significant portion of the interior of the appurtenance 120. The configuration of projections 200 A, B, C, D and E spaced apart on the appurtenance 120, of different lengths and extending at different angles, $\theta_1$, $\theta_2$, $\theta_3$, $\theta_4$, $\theta_5$ results in an appurtenance 120 that can sample fluid present in different regions and layers of the wound dressing layer 220. The plurality of projections 200 A, B, C, D and E can each be attached to an individual fluid-activated voltaic cell which are in turn connected to individual transmission units (e.g. as illustrated in FIG. 10). The plurality of projections 200 A, B, C, D and E can each be attached to an individual fluid-activated voltaic cell which are all connected to one transmission unit (e.g. as illustrated in FIG. 11). The plurality of projections 200 A, B, C, D and E can each be attached to a single fluid-activated voltaic cell connected to a corresponding transmission unit (see FIG. 7). There can be combinations of projections attaching to the same or different fluid-activated voltaic cells, which can in turn be attached to one or more transmission units. A plurality of projections 200 A, B, C, D and E included on a single appurtenance can be of varying shapes, sizes, and widths. A plurality of projections 200 A, B, C, D and E included on a single appurtenance can be configured to allow fluid flow through the projections at different rates, for example with conduits of different internal dimensions.

A configuration of projections including projections of varying lengths, varying positional spacing, and extending at different angles can be configured to sample different regions of a wound dressing. Various configurations can be utilized for particular medical monitoring requirements. For example, one or more projections can be configured to extend into a region of the wound dressing adjacent to a periwound region to monitor fluid in that region of the dressing. A caregiver may wish to maintain low moisture content in the region of the wound dressing adjacent to the periwound region, for example to minimize maceration and associated tissue damage. In such a situation, an appurtenance with multiple projections of a size and shape to extend into the region of the specific wound dressing adjacent to the periwound region for a particular patient can be selected. If fluid becomes abundant in the region of the wound dressing adjacent to the periwound region, the fluid will flow through the projection and act as an electrolyte in an attached fluid-activated voltaic cell. The resulting current will activate a transmission unit attached to the attached fluid-activated voltaic cell, resulting in a signal transmission and subsequent notification of a caregiver that the wound dressing should be manually checked. For example, an appurtenance with a plurality of projections of different discrete lengths can be utilized to sample fluid potentially present at different horizontal levels of a wound dressing. A caregiver may wish to be notified sequentially of the level of fluid present in a particular deep dressing, for example if a wound bleeds through the entire depth of the dressing over time. An appurtenance with a plurality of projections of different discrete lengths can be utilized to monitor fluid potentially present in the different layers, and to utilize current generated from a plurality of fluid-activated voltaic cells to power one or more transmission units over time. Information from the resulting series of signals (e.g. time of receipt, time between signals, elapsed time from wound dressing application) can be stored in memory at a remote unit for processing and notification of a caregiver. For more general monitoring of fluid presence in a wound dressing, an appurtenance with a plurality of projections spaced apart on the appurtenance, the projections of different lengths and extending at different angles (e.g. as illustrated in FIG. 12) can be employed to monitor a majority of the interior region of the wound dressing.

FIG. 13 illustrates aspects of a system including a wound dressing with an affixed appurtenance combination unit 125. As shown in FIG. 12, a wound dressing with an affixed appurtenance combination unit 125 is placed over a wound on a body part 110 of a patient. For example, the body part 110 can have been subject to a surgery, and therefore to have an acute wound. For example, the body part 110 can include an ulcer, and therefore have a chronic wound. The wound dressing with an affixed appurtenance combination unit 125 transmits signals 1340 to the local unit 1310. The wound dressing with an affixed appurtenance combination unit 125 is configured to transmit signals 1340 in response to an electrochemical reaction generating a current within a fluid-activated voltaic cell of the appurtenance.

A local unit 1310 can include a handheld device. For example, the local unit 1310 can include a distinct handheld device. For example, the local unit 1310 can be included as part of a larger handheld unit, for example a computing tablet, a laptop, a cell phone, a personal communication device, or similar types of devices. A local unit 1310 can be configured to be attached to a location, such as the end of a hospital bed, a medical stand, a bedside table, a wheelchair, or similar device. A local unit 1310 can be configured to be integrated into a piece of mobile equipment, such as the end of a hospital bed, a medical stand, a wheelchair, or similar device. For example, a local unit can be integrated with a medical cart, as described in U.S. Pat. No. 7,667,606 to Packert et al., titled "RF Enabled Surgical Cart and Use of Same in Operating Room Environment," which is incorporated herein by reference. A local unit 1310 can be configured to be integrated into a furnishing. For example, a local unit 1310 can be integrated into a hospital bed, a bedside hospital monitor, a bedside table, a medical chair, a medical table, or similar furnishing. A local unit 1310 can include a display unit 1320. In some embodiments, there can be a secondary device configured to relay signals from a wound dressing with an affixed appurtenance combination unit 125 to the local unit 1310, for example as described in U.S. Pat. No. 7,986,235 to Posamentier titled "RFID Receive-Only System," which is incorporated herein by reference. For example, a secondary device configured to relay signals from a wound dressing with an affixed appurtenance combination unit 125 to the local unit 1310 can be configured to increase the signal strength to a local unit 1310 positioned a distance away from the wound dressing with an affixed appurtenance combination unit 125. For example, a secondary device configured to relay signals from a wound dressing with an affixed appurtenance combination unit 125 to the local unit 1310 can be configured to relay signals from a plurality of wound dressings with affixed appurtenance units 125 to a single local unit 1310. A local unit 1310 can include an input device 1330, for example a keyboard. Although the local unit 1310 illustrated in FIG. 13 includes a keyboard as an input device 1330, in some embodiments the input device 1330 can include other types of input devices, for example a touchscreen, stylus, keypad, or voice recognition system. The local unit 1310 can include memory, including memory configured to store information relating to signals received from one or more combination units 125. Although not illustrated in FIG. 13, a local unit 1310 can transmit signals to a central assembly, such as through wireless or a wired connection. A user 1300, such as a medical caregiver, operates the local unit 1310.

A user 1300 can include a medical caregiver, such as a nurse or doctor, or a patient or other individual monitoring the wound dressing. Although user 1300 is shown/described herein as a single illustrated figure, those skilled in the art will appreciate that user 1300 can be representative of a human user, a robotic user (e.g., computational entity), and/or substantially any combination thereof (e.g., a user can be assisted by one or more robotic agents) unless context dictates otherwise. Those skilled in the art will appreciate that, in general, the same can be said of "sender" and/or other entity-oriented terms as such terms are used herein unless context dictates otherwise. A user 1300 can utilize a local unit 1310 through a user interface, for example one or more buttons, a keyboard, a touchscreen, a voice recognition device, a stylus, or other means.

A local unit 1310 can be configured to monitor for signals to one or more wound dressings with attached appurtenances 125 automatically. The signals 1340 sent from the wound dressing with attached appurtenance unit 125 to the local unit 1310 can be radio frequency signals in a particular wavelength, or range of wavelengths. For example, the signals can be in the UHF range, such as a UHF sub-range commonly used in a particular geographic region. See, for example the "Worldwide RFID UHF Map" by Intelleflex Corporation (©2009), which is incorporated herein by reference. For example, the signals can be in a range specified by an industry standard. For example, the signals can be in the approximately 13.56 megahertz (MHz) range, or within the ISO 14443 standard parameters. For example, the signals can be in the IEEE 802.11x standard or the Bluetooth standard range. See, for example, U.S. Pat. No. 7,215,976 to Brideglall, titled "RFID Device, System and Method of Operation Including a Hybrid backscatter-based RFID Protocol Compatible with RFID, Bluetooth and/or IEEE 802.11x Infrastructure," which is incorporated herein by reference. For example, the signals can be in the approximately 131 kilohertz (KHz) range, for example as part of a RuBee™ (IEEE standard 1902.1) system (i.e. equipment sold by Visible Assets™, Inc.). See for example: the description of RuBee™ systems from the Visible Assets™ webpage; Stevens et al., "RuBee (IEEE 1902.1)—The Physics Behind, Real-Time, High Security Wireless Asset Visibility Networks in Harsh Environments," a white paper from Visible Assets™; and in US Patent Application No. 2007/0171076 to Stevens and Waterhouse, titled "Low-frequency Radio Tag Encapsulating System," each of which are incorporated herein by reference.

In some embodiments, the wound dressing with attached appurtenance unit 125 includes a backscatter or reflective transmission device, and so the signals 1340 sent from the wound dressing with attached appurtenance unit 125 to the local unit 1310 can include backscatter or reflective signals. For example, as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference.

The signals 1340 transmitted from the wound dressing with attached appurtenance combination unit 125 can be sent in a fixed direction from the transmission source. The wound dressing with attached appurtenance combination unit 125 and the local unit 1310 can each include markings or other visible aspects directing a user how as to orient the wound dressing with attached appurtenance combination unit 125 and the local unit 1310 relative to each other for signal directionality.

In many embodiments, it is envisioned that the signal strength of a signal 1340 transmitted from the wound dressing with attached appurtenance combination unit 125 will be such that the signal 1340 will not travel a significant distance. The local unit 1310 and the wound dressing with attached appurtenance combination unit 125 can, therefore, need to be placed in reasonably close proximity for signals 1340 to travel between the devices. For example, the signal 1340 transmitted from the wound dressing with attached appurtenance combination unit 125 can be such that the receiver of such signals should be within the same room. For example, the signal 1340 transmitted from the wound dressing with attached appurtenance combination unit 125 can be such that the receiver of such signals should be within 10 feet. For example, the signal 1340 transmitted from the wound dressing with attached appurtenance combination unit 125 can be such that the receiver of such signals should be within 3 feet.

Figure 14:
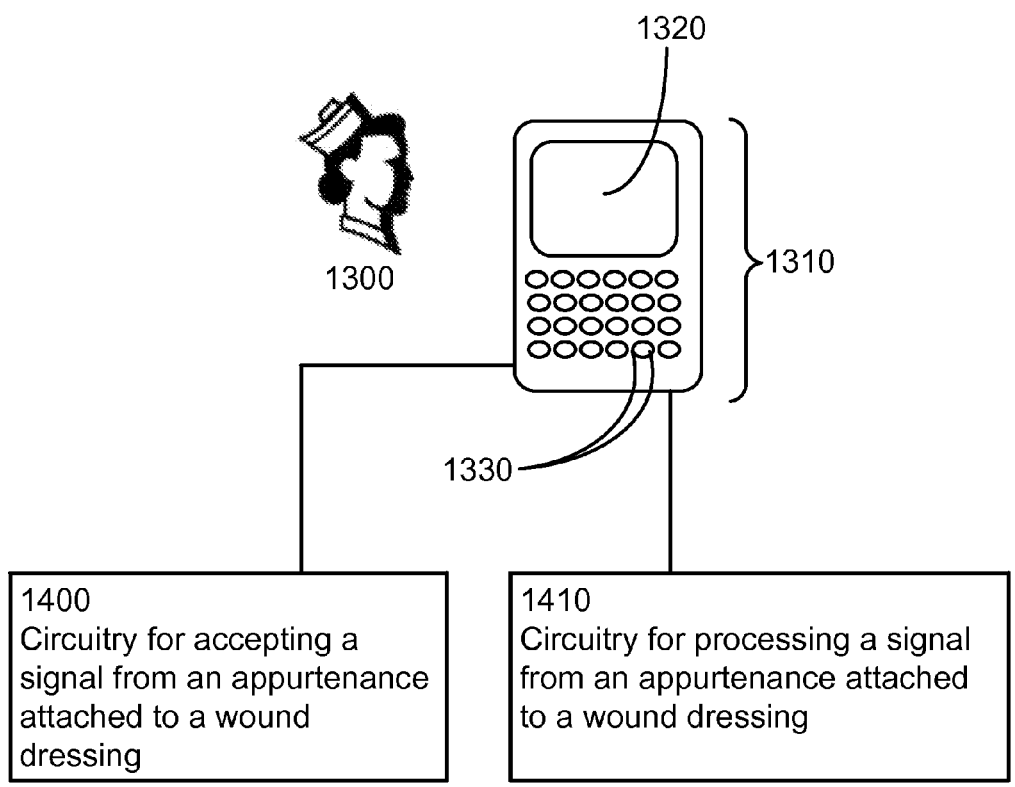
FIG. 14 is a depiction of a local unit.

FIG. 14 illustrates aspects of a local unit 1310. As shown in FIG. 14, a local unit 1310 includes a display unit 1320 and a input device 1330. A user 1320 operates the local unit 1310. The local unit 1310 includes circuitry for accepting a signal from an appurtenance attached to a wound dressing 1400. The local unit 1310 includes circuitry for processing a signal from an appurtenance attached to a wound dressing 1410.

In some embodiments, an appurtenance to a wound dressing includes an appurtenance configured to attach to a wound dressing, the appurtenance including a conduit configured to allow fluid flow from an interior region of a wound dressing into the appurtenance; a fluid-activated voltaic cell including an internal chamber, the internal chamber attached to the conduit; and a radio frequency identification (RFID) unit attached to the fluid-activated voltaic cell and configured to operate in response to current generated by the fluid-activated voltaic cell. The internal chamber can be configured to receive the fluid flowing through the conduit. The conduit can include a plurality of microchannels configured to direct fluid flow into the fluid-activated voltaic cell. See, for example, U.S. Pat. No. 6,420,622 to Johnston, "Medical Article Having Fluid Control Film," which is incorporated by reference herein. The RFID unit can include a unique identifier for that unit. The RFID unit can include an antenna, and circuitry configured to initiate signal transmission from the antenna. The RFID unit can include a processor. Some embodiments also include a second conduit positioned to allow fluid flow from a second interior region of a wound dressing into the appurtenance; and a second fluid-activated voltaic cell including an internal chamber, the internal chamber attached to the second conduit, wherein the second fluid-activated voltaic cell is configured to direct current to the RFID unit. Some embodiments also include a sensor attached to the conduit; and a connector between the sensor and the RFID unit.

A method of monitoring a wound includes the steps of: conveying fluid from an interior region of a wound dressing to an appurtenance of the wound dressing; placing the fluid adjacent to a first electrode and a second electrode of a fluid-activated voltaic cell integral to the appurtenance; and utilizing current received from the fluid-activated voltaic cell directly to send a wireless signal beyond the appurtenance. For example, a transmission unit connected to the fluid-activated voltaic cell integral to the appurtenance can send a wireless signal beyond the appurtenance in response to the current generated by the fluid-activated voltaic cell.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which can vary. Optical aspects of implementations will typically employ optically-oriented hardware, software, and or firmware.

In some implementations described herein, logic and similar implementations can include software or other control structures. Electronic circuitry, for example, can have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations can include executing a special-purpose instruction sequence or invoking circuitry for enabling, triggering, coordinating, requesting, or otherwise causing one or more occurrences of virtually any functional operations described herein. In some variants, operational or other logical descriptions herein can be expressed as source code and compiled or otherwise invoked as an executable instruction sequence. In some contexts, for example, implementations can be provided, in whole or in part, by source code, such as C++, or other code sequences. In other implementations, source or other code implementation, using commercially available and/or techniques in the art, can be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) can be manifested as a Verilog-type hardware description (e.g., via Hardware Description Language (HDL) and/or Very High Speed Integrated Circuit Hardware Descriptor Language (VHDL)) or other circuitry model which can then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, the various embodiments described herein can be implemented, individually and/or collectively, by various types of electro-mechanical systems having a wide range of electrical components such as hardware, software, firmware, and/or virtually any combination thereof; and a wide range of components that can impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context can dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof. At least a portion of the devices and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

The herein described components (e.g., operations), devices, objects, and the discussion accompanying them are used as examples for the sake of conceptual clarity and that various configuration modifications are contemplated. Consequently, as used herein, the specific examples set forth and the accompanying discussion are intended to be representative of their more general classes. In general, use of any specific example is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, changes and modifications can be made without departing from the subject matter described herein and its broader aspects and, therefore, the appended claims are to encompass within their scope all such changes and modifications as are within the true spirit and scope of the subject matter described herein. Terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim lncludes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the recited operations therein can generally be performed in any order. Also, although various operational flows are presented in a sequence(s), it should be understood that the various operations can be performed in other orders than those which are illustrated, or can be performed concurrently. Examples of such alternate orderings can include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

EXAMPLE

An Appurtenance to a Wound Dressing Configured with a Fluid Activated Voltaic Cell to Detect and Report Fluid in a Wound Dressing in Real Time An appurtenance to a wound dressing is constructed from a flexible thin plastic substrate that is configured in a substantially planar shape (see FIG. 5). The appurtenance contains a transmission unit that includes: a microprocessor, memory, a transmitter, and an RFID antenna. The components are attached to a surface of the substrate with epoxy; and circuitry for the RFID are attached to the substrate with adhesive and connected to the antenna with conductive ink (e.g., polymer with flecks of silver) to create an operational RFID. A fluid activated voltaic cell is attached to the substrate and connected to the RFID with a wire connection. An aperture for a polyester tube with approximately 0.5 mm inside diameter is mounted in contact with the fluid activated voltaic cell (see FIG. 5) and attached to a polyester tube that projects away from the surface of the substrate for approximately 4 millimeters (mm). Encapsulating epoxy material is used to cover the components, the RFID circuitry, the conductive ink, conductive epoxy, the fluid activated voltaic cell and exterior of the tube port. A space is maintained around the edge of the polyester tube adjacent to the fluid activated voltaic cell under the encapsulating epoxy material. The space is configured to allow fluid to flow from the tube into contact with the fluid activated voltaic cell. The space is approximately 1 mm high and of sufficient lateral dimensions to cover the electrodes of the fluid activated voltaic cell (approximately 12 mm×12 mm).

Methods and circuitry to construct passive RFID tags are described (see e.g., U.S. Pat. No. 7,479,886 issued to Burr, "Antenna Capacitance for Energy Storage" and Chawla, "An Overview of Passive RFID," IEEE Applications & Practice, 11-17, (September 2007), which are each incorporated herein by reference). For example, the device can contain a dipole antenna of 22-gauge copper magnet wire, a rectifier to convert incoming UHF energy into DC, a capacitor to store the energy, and a programmable microcontroller (e.g., a MSP430™ microcontroller available from Texas Instruments, Dallas, Tex.) to perform sensing and computation (see e.g., Sample et al., "Design of an RFID-Based Battery-Free Programmable Sensing Platform," *IEEE Trans. Instr. Meas.* 57: 2608-2615, 2008 which is incorporated herein by reference). The RFID device can harvest energy from incoming radio waves or be empowered by current generated by the fluid activated voltaic cell.

A fluid activated voltaic cell serves as a moisture sensor and generates electrical current to empower the RFID device. A fluid activated voltaic cell is micro-fabricated from a silicon wafer with metallic layers serving as electrodes and wound fluids (e.g., exudate and blood) providing electrolyte to activate the voltaic cell. For example, a fluid activated voltaic cell can be constructed with magnesium, Mg, as the anode and silver chloride, AgCl, as the cathode (see e.g., Sammoura et al., *Sensors and Actuators A* 111: 79-86, 2004 and Lee et al., "Water Activated Disposable and Long Shelf Life Microbatteries," *Proceedings of IEEE Micro Electro Mechanical Systems Conference*, pp. 387-390, Kyoto, Japan, January 2003 which are incorporated herein by reference). A fluid activated voltaic cell is fabricated from silicon wafers by depositing a layer of Mg on a top substrate and AgCl on a bottom substrate and creating a gap of approximately 50 µm between the Mg and AgCl layers using spacers. A layer of chromium/gold is deposited under the AgCl layer to collect electrons from the voltaic cell. A voltaic cell approximately 12 mm×12 mm produces a maximum output voltage of approximately 1.65 Volts with a voltaic cell capacity of approximately 1.8 mWatt-hours when the cell is activated with a drop of water, approximately 40 µL, and discharged under a resistance of 1 kilohm. This corresponds to reaching a maximum voltage of 1.6 V within a minute of activation and maintaining this level for approximately 20 minutes followed by a gradual decline to 0.6 V over the next 40 minutes. The output voltage of the fluid activated cell may be increased by providing enhancers that promote the electromotive force of the cell. For example, an enhancer of desiccated acid can be included in the electrochemical cell to produce acidic fluid and increase the voltage produced by the cell when fluid enters the cell (see e.g., Goodisman, "Observation on Lemon Cells", *J. Chem. Ed.* 78: 516-518, 2001 which is incorporated herein by reference). The provision of solid citric acid as an enhancer which dissolves upon contact with wound fluids can lower the pH of the fluid within the cell to approximately 3.0 and increase the electromotive force of the cell by increasing the dissolution of Mg (see e.g., Goodisman, Ibid.).

The substrate of the appurtenance is attached to the outer surface of a wound dressing with adhesive. A styrene copolymer pressure-sensitive adhesive can be used. In addition, the distal end of the polyester tube is pressed into the layers of the wound dressing with finger-tip pressure. The wound dressing is of sufficient thickness so as to maintain the end of the polyester tube within the layers of the wound dressing, allowing for both the length of the tube itself and the angle it projects from the substrate. For example, if the tube is 4 mm long, the wound dressing can be 6 mm thick, or greater. For example, if the tube is 4 mm long, the wound dressing can be 4 mm thick if the tube is placed at a sufficient angle to maintain the distal end of the tube within the wound dressing. The wound dressing with the appurtenance is placed immediately over the wound and the RFID identity number, patient information, the time and date are entered into a central computer system after interrogating the RFID tag with a RFID reader in a local unit and accessing the patient's electronic medical record. If the patient is wearing an RFID identification device (such as a wristband with an embedded RFID unit) the patient information can be input into the system by scanning the identification device in association with scanning the appurtenance.

The fluid activated voltaic cell is in fluid communication with the lower portion of the appurtenance relative to the insertion point into the wound dressing. For example, the voltaic cell is located adjacent to an opening in the enclosure and is used to monitor the amount of fluids that emanate from the wound and flow through the projection tube by capillary action. Wound moisture levels are correlated with healing, and a rapid increase in moisture level can indicate a microbial infection is present (see e.g., U.S. Pat. No. 6,963,772 to Bloom et al., "User-Retainable Temperature and Impedance Monitoring Methods and Devices," which is incorporated herein by reference). Wound fluid entering the aperture activates the fluid activated voltaic cell which can yield approximately 1.8 mW-hours power (see e.g., Sammoura et al., Ibid.) to empower the RFID device which can operate with approximately 600 μW of power (see e.g., Sample et al., Ibid.). The empowered RFID device transmits a UHF signal which is received by a local unit proximal to the patient.

A RFID reader in a local unit (for example, a cell phone) proximal to the patient (e.g., on the edge of the patient's hospital bed or on a bedside table) receives the UHF signal from the RFID device. The UHF signal encodes information such as the patient's identity, the patient's room number, the identification number and location of the appurtenance, and the day and time of the signal transmission. The local unit responds by transmitting signals at the bedside to alert the patient and to a central computer to notify healthcare personnel. For example the local unit can signal at the bedside by emitting an audible alarm, and transmit wirelessly to a central computer which can notify caregivers, for example, through a message sent to the nursing station. The local unit can also indicate to a healthcare worker the need to change a wound dressing based on the elapsed time since the wound dressing was applied (i.e. when the appurtenance was first "read" into the system). Moreover the local unit transmission to a central computer creates a record in the patient's electronic health record which includes all of the information transmitted by the local unit relating to that appurtenance and any other appurtenances utilized by the same patient over time.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An appurtenance to a wound dressing, comprising:
a substrate configured to attach to a wound dressing;
a fluid-activated voltaic cell attached to the substrate, the fluid-activated voltaic cell including an internal region having at least two electrodes, the internal region of the fluid-activated cell being configured to receive a fluid from an interior region of the wound dressing, the fluid-activated voltaic cell being further configured to generate electrical power from interaction of the fluid with the at least two electrodes;
a transmission unit attached to a surface of the substrate, the transmission unit including circuitry and at least one antenna, the transmission unit configured to transmit a signal in response to the electrical power generated by the fluid-activated voltaic cell; and
a projection operably attached to the fluid-activated voltaic cell, the projection of a size and shape to extend into the interior region of the wound dressing and configured to channel the fluid from within the interior region of the wound dressing to the internal region of the fluid-activated voltaic cell.

2. The appurtenance of claim 1, wherein the fluid-activated voltaic cell comprises:
at least one enhancement unit configured to release at least one chemical enhancer of an electrochemical reaction within the fluid-activated voltaic cell in response to contact with the fluid.

3. The appurtenance of claim 2, wherein the at least one enhancement unit comprises:
at least one dry acid unit configured to release an acid when contacted by a liquid.

4. The appurtenance of claim 1, wherein the fluid-activated voltaic cell comprises:
a chamber defining at least a portion of the interior region.

5. The appurtenance of claim 1, wherein the transmission unit comprises:
a radio frequency identification (RFID) unit.

6. The appurtenance of claim 1, wherein the transmission unit comprises:
a near field communication (NFC) unit.

7. The appurtenance of claim 1, wherein the transmission unit comprises:
a unique identifier.

8. The appurtenance of claim 1, wherein the transmission unit comprises:
a processor.

9. The appurtenance of claim 1, wherein the projection comprises:
at least one substantially hollow tube with a first aperture at a location adjacent to the interior region of the wound dressing and a second aperture at a location adjacent to a surface of the fluid-activated voltaic cell.

10. The appurtenance of claim 1, wherein the projection comprises:
a plurality of apertures located along a length of the projection; and
a plurality of conduits, each conduit including a first end attached to one of the plurality of apertures, and a second end attached to the fluid-activated voltaic cell, each conduit configured to direct the fluid from the interior region of the wound dressing into the fluid-activated voltaic cell.

11. The appurtenance of claim 1, wherein the projection is partially positioned within the fluid-activated voltaic cell, and wherein the projection includes an aperture within the fluid-activated voltaic cell.

12. The appurtenance of claim 1, comprising:
a wire connector between the fluid-activated voltaic cell and the transmission unit.

13. The appurtenance of claim 1, comprising:
a passive radio frequency identification (RFID) unit including an identifier.

14. The appurtenance of claim 1, comprising:
a second fluid-activated voltaic cell attached to the substrate and configured to activate the transmission unit; and
a second projection operably attached to the second fluid-activated voltaic cell, the second projection configured to sample a second fluid within a second interior region of the wound dressing.

15. The appurtenance of claim 1, comprising:
a sensor connected to the transmission unit.

16. An appurtenance to a wound dressing, comprising:
an enclosure of a height and width to fit substantially within an interior region of a wound dressing, the enclosure including at least one aperture configured to allow a fluid to flow from the interior region of the wound dressing into the enclosure;
a fluid-activated voltaic cell attached to the at least one aperture, the fluid-activated voltaic cell including an internal region having at least two electrodes, the internal region of the fluid-activated cell being configured to receive the fluid from the at least one aperture, the fluid-activated voltaic cell being further configured to generate electrical power from interaction of the fluid with the at least two electrodes; and
a transmission unit attached to an internal surface of the enclosure, the transmission unit including circuitry and at least one antenna, the transmission unit configured to transmit a signal in response to the electrical power generated by the fluid-activated voltaic cell.

17. The appurtenance of claim 16, wherein the enclosure comprises:
a substantially cylindrical structure, wherein a largest width of the substantially cylindrical structure is less than a smallest width of the wound dressing.

18. The appurtenance of claim 16, wherein the enclosure comprises:
a substantially pyramidal structure, wherein a largest width of the substantially pyramidal structure is less than a smallest width of the wound dressing.

19. The appurtenance of claim 16, wherein the enclosure comprises:
one or more walls, the walls forming a flange on an edge of the enclosure, the flange positioned to attach a fastener between a surface of the wound dressing and the enclosure.

20. The appurtenance of claim 16, wherein the enclosure comprises:
one or more walls, the walls forming a flange on an edge of the enclosure, the flange including one or more projections from a surface of the flange, the one or more projections positioned to pierce an outer surface of the wound dressing.

21. The appurtenance of claim 16, wherein the enclosure comprises:
a substantially hollow tube.

22. The appurtenance of claim 16, wherein the enclosure comprises:
a plurality of apertures.

23. The appurtenance of claim 16, wherein the at least one aperture of the enclosure comprises:
a micro-capillary film configured to direct the fluid from the interior region of the wound dressing into an interior of the enclosure.

24. The appurtenance of claim 16, wherein the at least one aperture of the enclosure comprises:
a conduit configured to direct the fluid from the interior region of the wound dressing into an internal region of the fluid-activated voltaic cell.

25. The appurtenance of claim 16, wherein the fluid-activated voltaic cell comprises:
at least one enhancement unit configured to release at least one chemical enhancer of an electrochemical reaction within the fluid-activated voltaic cell in response to contact with the fluid.

26. The appurtenance of claim 25, wherein the at least one enhancement unit comprises:
at least one dry acid unit configured to release acid when contacted by a liquid.

27. The appurtenance of claim 16, wherein the fluid-activated voltaic cell comprises:
a chamber defining at least a portion of the interior region.

28. The appurtenance of claim 16, wherein the transmission unit comprises:
a radio frequency identification (RFID) unit.

29. The appurtenance of claim 16, wherein the transmission unit comprises:
a near filed communication (NFC) unit.

30. The appurtenance of claim 16, wherein the transmission unit comprises:
a unique identifier.

31. The appurtenance of claim 16, wherein the transmission unit comprises:
a processor.

32. The appurtenance of claim 16, comprising:
a wire connector between the fluid-activated voltaic cell and the transmission unit.

33. The appurtenance of claim 16, comprising:
a passive radio frequency identification (RFID) unit including an identifier.

34. The appurtenance of claim 16, comprising:
a second fluid-activated voltaic cell attached to at least one second aperture, the at least one second aperture configured to allow a fluid to flow from a second interior region of the wound dressing into an interior of the second fluid-activated voltaic cell.

35. The appurtenance of claim 16, comprising:
a sensor attached to the at least one aperture of the enclosure; and
a connection between the sensor and the transmission unit.

36. An appurtenance to a wound dressing, comprising:
an appurtenance configured to attach to a wound dressing, the appurtenance including a conduit configured to allow a fluid to flow from an interior region of the wound dressing into the appurtenance;

a fluid-activated voltaic cell including an internal chamber, the internal chamber including at least two electrodes, the internal chamber being attached to the conduit and being configured to receive the fluid from the interior region of the wound dressing, the fluid-activated voltaic cell being further configured to generate electrical power from interaction of the fluid with the at least two electrodes; and a radio frequency identification (RFID) unit attached to the fluid-activated voltaic cell and configured to operate in response to the electrical power generated by the fluid-activated voltaic cell.

37. The appurtenance of claim 36, wherein the appurtenance is configured to attach to an exterior surface of the wound dressing.

38. The appurtenance of claim 36, wherein the conduit comprises:
a plurality of microchannels configured to direct the fluid to flow into the fluid-activated voltaic cell.

39. The appurtenance of claim 36, wherein the conduit comprises:
at least one projection, the projection including at least one aperture positioned distal to the appurtenance, the projection configured to allow the fluid to flow from the interior region of the wound dressing into the appurtenance.

40. The appurtenance of claim 36, wherein the fluid-activated voltaic cell comprises:
at least one enhancement unit configured to release at least one chemical enhancer of an electrochemical reaction within the fluid-activated voltaic cell in response to contact with the fluid.

41. The appurtenance of claim 40, wherein the at least one enhancement unit comprises:
at least one dry acid unit configured to release an acid when contacted by a liquid.

42. The appurtenance of claim 36, wherein the fluid-activated voltaic cell comprises:
a chamber attached to the conduit, the chamber configured to receive the fluid.

43. The appurtenance of claim 36, wherein the radio frequency identification (RFID) unit comprises:
a unique identifier.

44. The appurtenance of claim 36, wherein the radio frequency identification (RFID) unit comprises:
an antenna; and
circuitry configured to initiate a signal transmission from the antenna.

45. The appurtenance of claim 36, wherein the radio frequency identification (RFID) unit comprises:
a processor.

46. The appurtenance of claim 36, comprising:
a second conduit positioned to allow the fluid to flow from a second interior region of the wound dressing into the appurtenance; and
a second fluid-activated voltaic cell including a second internal chamber, the second internal chamber attached to the second conduit, wherein the second fluid-activated voltaic cell is configured to direct current to the radio frequency identification (RFID) unit.

47. The appurtenance of claim 36, comprising:
a sensor attached to the conduit; and
a connector between the sensor and the radio frequency identification (RFID) unit.

* * * * *